United States Patent
Berg et al.

(10) Patent No.: US 7,602,497 B2
(45) Date of Patent: Oct. 13, 2009

(54) REFLECTANCE SENSOR FOR MEASURING LIQUID PIGMENT PREPARATIONS OR SOLID PIGMENTED SURFACES

(75) Inventors: Jan Berg, Münster (DE); Jürgen Lohmann, Münster (DE); Michael Schäfer, Altrip (DE); Jürgen Ettmüller, Hassloch (DE)

(73) Assignee: BASF Coatings AG, Munster (DE)

( * ) Notice: Subject to any disclaimer, the term of this patent is extended or adjusted under 35 U.S.C. 154(b) by 239 days.

(21) Appl. No.: 10/559,545

(22) PCT Filed: Jul. 1, 2004

(86) PCT No.: PCT/EP2004/007141

§ 371 (c)(1),
(2), (4) Date: Mar. 28, 2006

(87) PCT Pub. No.: WO2005/003740

PCT Pub. Date: Jan. 13, 2005

(65) Prior Publication Data

US 2007/0058171 A1 Mar. 15, 2007

(30) Foreign Application Priority Data

Jul. 7, 2003 (DE) .................................. 103 30 641

(51) Int. Cl.
*G01N 21/47* (2006.01)
(52) U.S. Cl. ...................................... 356/446; 356/416
(58) Field of Classification Search ................. 356/410, 356/445–446, 246
See application file for complete search history.

(56) References Cited

U.S. PATENT DOCUMENTS

| 3,773,424 | A | * | 11/1973 | Selgin ......................... 356/410 |
| 3,885,878 | A | * | 5/1975 | Ishak .......................... 356/405 |
| 4,029,419 | A | | 6/1977 | Tong et al. ................... 356/173 |
| 4,033,698 | A | | 7/1977 | Demsky et al. .............. 356/173 |
| 4,936,685 | A | * | 6/1990 | Taylor et al. ................. 356/246 |
| 6,583,878 | B2 | * | 6/2003 | Hustert ........................ 356/402 |
| 2002/0131043 | A1 | * | 9/2002 | Steenhoek et al. ........... 356/328 |
| 2002/0149773 | A1 | * | 10/2002 | Martino et al. .............. 356/436 |
| 2008/0019887 | A1 | * | 1/2008 | Lohmann et al. ............ 422/243 |

FOREIGN PATENT DOCUMENTS

| EP | 0 472 899 | 7/1991 |
| WO | WO 98/16822 | 4/1998 |
| WO | WO 02/075285 | 9/2002 |

OTHER PUBLICATIONS

English Abstract for EP 0 472 899, Publication date Mar. 4, 1992.

* cited by examiner

*Primary Examiner*—Kara E Geisel
(74) *Attorney, Agent, or Firm*—Cantor Colburn LLP

(57) ABSTRACT

The invention relates to reflectance sensors built up from an optical unit, a sample analysis unit and a system control unit, and to a method of measuring the reflectance of a sample in the form of a liquid pigment preparation, and to the use of a reflectance sensor according to the invention for the measurement of the reflectance of liquid pigment preparations in various process stages during the production, further processing and use of the liquid pigment preparations.

15 Claims, 12 Drawing Sheets

REFLECTANCE SENSOR FOR MEASURING LIQUID PIGMENT PREPARATIONS OR SOLID PIGMENTED SURFACES

CROSS REFERENCE TO RELATED APPLICATIONS

This application is a National Phase Application based on PCT/EP2004/007141, filed on 1 Jul. 2004, which claims priority to DE 103 30 64.2, filed 7 Jul. 2203.

BACKGROUND OF THE INVENTION

The invention relates to reflectance sensors built up from an optical unit, a sample analysis unit and a system control unit, and to a method of measuring the reflectance of a sample in the form of a liquid pigment preparation, and to the use of a reflectance sensor according to the invention for the measurement of the reflectance of liquid pigment preparations in various process stages during the production, further processing and use of the liquid pigment preparations.

During the production of liquid pigment preparations such as paint or enamel mixtures, pigment pastes, white let-downs or other color mixtures, a reproducible color and hiding power of the mixtures is important. This reproducibility is ensured by regular product control during the production of the liquid pigment preparations, either visually or with the aid of spectroscopic methods. According to the prior art, control is carried out by mixing the desired color mixtures, applying to a substrate and drying, curing or stoving and subsequent analysis of the colored layers obtained. Although this method is accurate, it is very time-consuming.

A significant saving in time can be achieved by the measurement being carried out directly on the liquid pigment preparations, so that application of colored layers to the substrate and subsequent drying of the layers is not required.

In principle, all commercial color measuring instruments are suitable for this task. Each VIS sensor which operates in reflectance is likewise suitable for this.

For example, EP-A 0 472 899 relates to a photometric measuring device for measuring the level of attenuation during the propagation of light in disperse systems. This device is built up from a through-flow cuvette for the sample to be examined, with at least one lateral opening for the optical connection of at least one optical waveguide. From a light source, an optical waveguide connection leads to the interior of the cuvette with the sample to be examined and from there to an optical detector to generate a measured signal. A direct optical waveguide connection leads directly from the light source to the optical detector to generate a reference signal. Furthermore, the photometric device comprises an evaluation device connected to the optical detector.

WO 98/16822 relates to an analysis system for the analysis of the physical properties of coatings, pigment pastes or similar systems, which is built up from an apparatus for forming a film of the coatings, pigment pastes and similar systems with a specific thickness, a light source for irradiating the coating to be examined or pigment paste or similar systems to be examined, interaction occurring between the light and the coating, the pigment paste or similar system, a measured signal being generated; and from an apparatus for recording the measured signal and from a detector connected to the apparatus for picking up the measured signal.

Disadvantageous with these systems is the inadequate measurement accuracy which can be achieved with the measuring arrangements known from the prior art.

SUMMARY OF THE INVENTION

An object of the present invention is therefore a reflectance sensor and a method of measuring the reflectance of products which is distinguished by high measurement accuracy and reliably provides suitable measured data for determining the color and hiding power of the liquid pigment preparations, and the provision of various methods of measuring the reflectance of pigment preparations by using the measuring method according to the invention.

Colorimetry per se is prior art. If this procedure is explained here, this is only to make it clear that this sensor is suitable for all these methods. A reflectance measurement initially supplies the reflectance spectrum of the product, which is then referred to the reflectance spectrum of a white standard. From this normalized reflectance, the Lab values also frequently used to describe color can then be calculated. A reflectance measurement does not supply the hiding power directly, or what is known as the absorption and scattering spectrum of a pigment preparation. However, by measuring the preparation in a non-hiding layer thickness over black and over white, or by measuring series of white let-downs and black let-downs, these values can be determined.

This object is achieved by a reflectance sensor (embodiment (I)) built up from
a) an optical unit (A) which comprises
   aa) a light source (Aa) in the form of a lamp, and
   ab) a fiber-optic system comprising optical waveguides (Ab), at least one optical waveguide being a reference waveguide,
b) a sample analysis unit (B), which comprises
   ba) a measuring window (Ba), and
   bb) a sample analysis cell (Bb),
   the optical unit being arranged on one side of the measuring window and the sample analysis cell being arranged on the other side of the measuring window, by said cell being pressed against the measuring window in such a way that, between measuring window and sample analysis cell, a gap is formed which must be traversed by a sample to be measured in the form of a liquid pigment preparation, the sample being sheared considerably as it traverses the gap, and
c) a system control unit (C) comprising detectors (Ca) for recording measured data and an evaluation device (Cb) connected thereto, at least one optical waveguide connection being led from the light source (Aa) to the measuring window (Ba) and from the measuring window (Ba) onward to the detector (Ca), to generate a measured signal (reflectance of product), and at least one reference waveguide connection being led directly from the light source (Aa) to the detector (Ca) or from the measuring window (Ba) to the detector (Ca) to produce a reference signal (internal reflection).

In the case of reflectance, the light which is reflected diffusely at the interface to the measuring window of a transparent two-dimensional element which terminates the optical waveguide is measured, but as a rule not the reflection from the interface itself. However, the latter forms an interfering background which, in general, lies between 1% and 0.001% of the white reflectance.

This means that the direct reflection of the illumination at the window should not be seen by the receiving fiber which receives the light scattered from the product, since this leads to a very high, undesired background component. However, the direct reflection can certainly be received in a further fiber and can be used as a monitor (additional or sole) of the illumination intensity. "Liquid pigment preparations" is to be understood to mean all pigment preparations which are suitable for reflectance measurement with the reflectance sensor according to the invention. The reflectance sensor of the invention is suitable for measuring liquid pigment preparations which are present, in various process stages in the production, further processing and use of the liquid pigment preparations. The reflectance sensor of the invention can, for example, be used to assess liquid pigment preparations during their production process or to assess the quality of the liquid pigment preparations during their use (for example for color matching in a painting system) or to monitor subsequent color changes of the liquid pigment preparations as a result of storage or shearing.

In this case, "color" is to be understood to mean the absorption+scatter of the pigment preparations. Typical "liquid pigment preparations" ("pigmented" preparation) are paints and colorants and also pastes, and coatings in general.

Such "liquid pigment preparations" are preferably paint or enamel mixtures, pigment pastes, white let-downs or other color mixtures or mixtures containing effect pigments such as micas or metallics, that is to say aluminum flakes, which are present in the form of a suspension or emulsion.

With a further embodiment (implement (II)) of a reflectance sensor according to the invention, it is also possible to measure the reflectance of pigmented solid surfaces such as plastics for moldings, plates (for example painted metal sheets) and films.

A further subject of the present invention is therefore a reflectance sensor (embodiment (II)), built up from
a) an optical unit (A) which comprises
   aa) a light source (Aa) in the form of a lamp, and
   ab) a fiber-optic system comprising optical waveguides (Ab), at least one optical waveguide being a reference waveguide,
b) a sample analysis unit (B'), which comprises
   b'a) a measuring window (B'a), and
   b'b) a holder for samples which have a solid surface (B'b),
and
c) a system control unit (C) comprising detectors (Ca) for recording measured data and an evaluation device (Cb) connected thereto, an optical waveguide connection being led from the light source (Aa) to the measuring window (B'a) and from the measuring window (B'a) onward to the detector (Ca), to generate a measured signal, and a reference waveguide connection being led directly from the light source (Aa) to the detector (Ca) or from the measuring window (B'a) to the detector (Ca) to produce a reference signal.

Considerable cost advantages result for many products if the reflectance can already be determined on the liquid preparation, in particular in the case of coatings.

The reflectance measurement on liquid products has an additional area of application since, even in the case of "other" products which are not immediately intended for the production of surfaces (as a coating or as the surface of a component), specific product and process properties can be determined from the reflectance, which can be interpreted in relation to the disperse state (for example particle size distribution, form, concentration) or to material properties (for example refractive index, crystal modification, chemical composition).

In this case, a distinction must be drawn as to whether these are conventional preparations (conventional coatings, "UNI" with isometric pigments or isometric "other" particles), or preparations with effect materials (for example metallics, that is to say aluminum flakes, or effect pigments such as micas or non-isometric, that is to say needle-like or platelet-like "other" particles), which are present in an aligned form following processing.

DETAILED DESCRIPTION a) Optical Unit (A)

Figure 1:
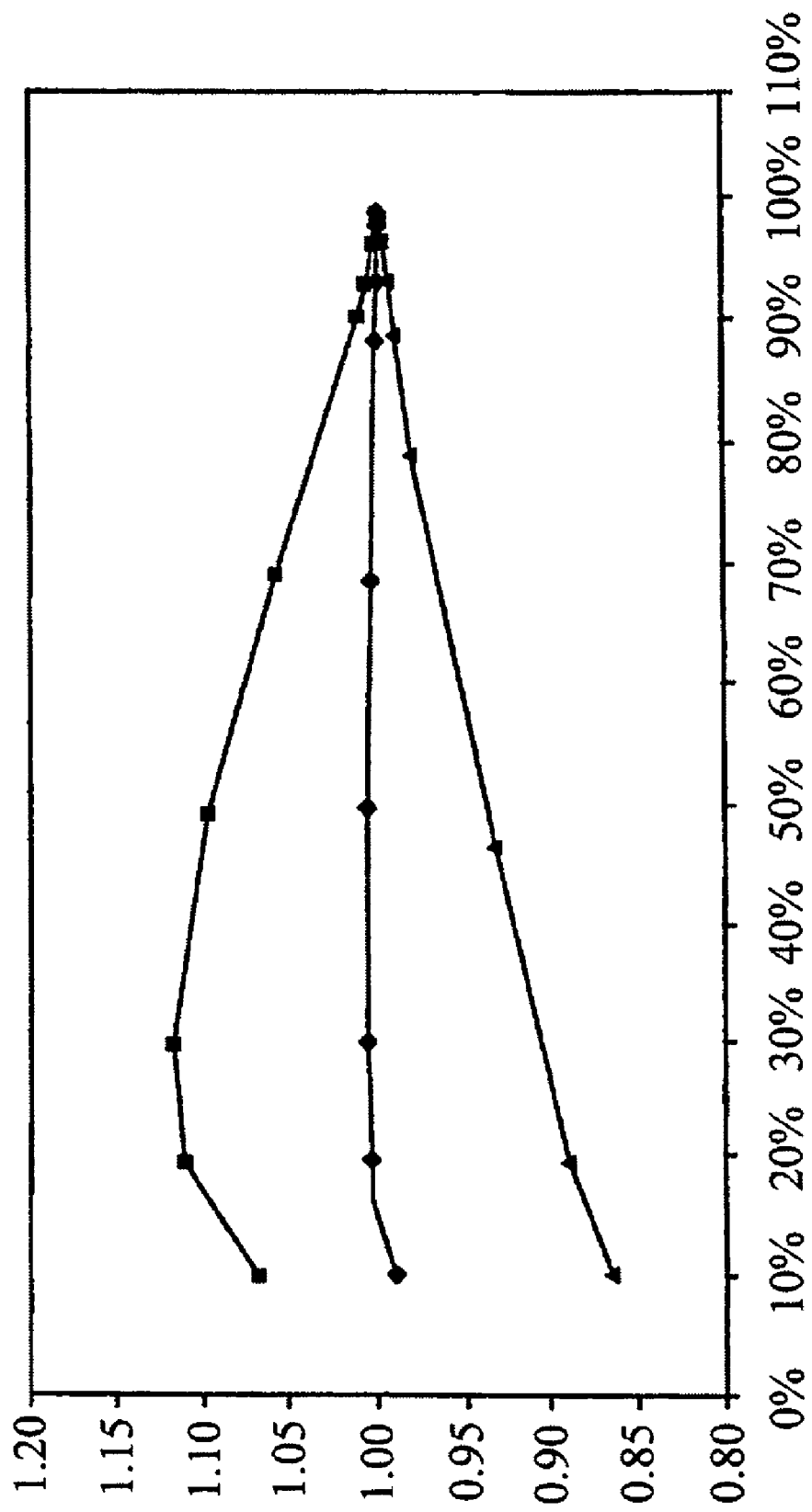
FIG. 1 illustrates characteristic curves for various sensor heads.

The optical unit has according to the invention one or more light sources (Aa) and the entire fiber-optic system (Ab). The features of the optical unit listed below apply both to the reflectance sensor according to the invention for measuring liquid pigment preparations (embodiment (I)) and to the reflectance sensor for measuring pigmented solid surfaces (embodiment (II)).

The light source must have a sufficient intensity and luminous intensity in order that a spectrometer can be operated in the range from 100 to 600 ms integration time. Furthermore, the spectrum of the lamp must be such that, in the case of white, all the wavelengths of the spectrometer are activated from 5% to 95%, preferably from 10% to 95% in the case of a lamp without correction and from 25% to 95% in the case of a lamp with correction. In this case, the highest possible percentages (in particular 95%) are particularly desirable. With the aid of color filters, the spectrum of the lamp can be improved further. These filters are able to "straighten" only lamp spectra which run flatly. Individual maxima which run very steeply, such as many gas discharge lamps have in great numbers, cannot be corrected.

Furthermore, temporal and spatial homogeneity is desirable. If a halogen lamp is used, it is preferably improved by defocusing and by means of a scattering disk. The aperture angle of the fiber (=optical waveguide) should be "filled with light" homogeneously. The fiber should not be curved too sharply. All improvement measures are at the cost of the intensity.

The light source is a lamp, for example LEDs, gas discharge lamps and lamps with incandescent filaments being suitable, a halogen lamp being preferred. A lamp with integrated shutter is particularly preferred. However, it is also possible to use other lamps which preferably have a spectrum, so that a dynamic of about 3 or less is achieved. At the same time, the lamp should exhibit low intensity fluctuations and sufficient brightness. The halogen lamp which is preferably used generally has a stabilized DC power supply.

Lamps with shutter operation are particularly preferred. In the case of sluggish light sources, such as an incandescent element (halogen) or gas discharge, this is achieved with a mechanical or, for example, optoelectronic shutter (possibilities known to those skilled in the art), in the case of fast light sources such as diodes or flash lamps, this is implemented by means of the electrical activation.

According to the present invention, preference is given to an arrangement in which a compensation filter is arranged behind the lamp, preferably a halogen lamp. In this case, "behind the lamp" is to be understood to mean the compensation filter is arranged downstream of the lamp, following the course of the light beam from the lamp. The compensation filter used in the preferred embodiment linearizes the spectrum from the lamp such that the difference between the highest and lowest intensity of the light emitted by the lamp is at most 4, preferably 3 to 4 and not 10 to 20, which is usual in the prior art. This is achieved by using multilayer filters made of commercially available filter glasses.

In a further preferred embodiment, an IR blocking filter, a condenser and a scattering disk are arranged behind the lamp, preferably halogen lamp, between lamp and compensation filter if a compensation filter is used, which is preferred. Once again, "behind the lamp" in the sense of the present application means downstream of the lamp, following the light beam. The IR blocking filter is used to reduce the heat loading which acts on the sample, the optical waveguides, the compensation filter and other units in the reflectance sensor as a result of the lamp.

The condenser is used to focus the light from the lamp onto the input of the fiber-optic system. The scattering disk is used to achieve a structure-free, uniform course of the brightness of the light from the lamp over the location and the aperture angle of the optical waveguides. Suitable designs of IR blocking filters, condensers and scattering disks which are suitable for the reflectance sensor according to the invention are known to those skilled in the art.

The shutter preferably integrated into the lamp, according to the invention, is preferably an electromechanical shutter which can darken the illuminations fiber completely. The darkening by means of the shutter is used to measure the dark current.

This means that the shutter interrupts the luminous flux from the lamp to the illumination fiber. This is required in order to measure the dark current of the spectrometer (this current always flows and, even in the case of complete darkness, leads to an indication), which must be subtracted from the measured value of the product. The spectrometer is erased by being read out, but only to about 99%, so that a residue of the last measurement remains in the spectrometer and distorts the first dark measurement. Beginning from the second successive dark measurement, the value is then undistorted.

The fiber-optic system of the reflectance sensor according to the invention comprises optical waveguides (=fibers). These fibers are one or more reference fiber(s), one or more receiving fiber(s) and one or more illumination fiber(s). In principle, embodiments which do not have any reference fiber(s) are also possible. However, the fiber-optic system normally comprises at least one reference fiber. The at least one reference fiber generally leads directly from the light source (Aa) to the detector (Ca). However, it is also possible for at least one reference fiber to lead from the measuring window (Ba) to the detector (Ca).

The use of a plurality of light sources increases the illumination intensity and, if different light sources are used, a more uniform illumination spectrum can be achieved. Each light source requires at least one illumination fiber and preferably at least one reference fiber in each case.

The optical waveguides are preferably fibers of 100, 200, 400, 600 or 800 μm fiber diameter. The fiber used as the reference waveguide particularly preferably has a diameter matched to, preferably smaller than, the remaining optical waveguides, since the lamp used, preferably a halogen lamp, itself has a high luminous intensity.

In order to achieve highly accurate measuring accuracies, in a preferred embodiment of the method according to the invention the optical waveguides are protected mechanically. For the purpose of mechanical protection, the optical waveguides are led in protective tubes and are supported over their entire length by means of a supporting frame. The protective tubes are generally made of conventional materials known to those skilled in the art, for example metal or polymer. The supporting frame is preferably a metal frame, to which the optical waveguides are fixed by means of conventional fixing materials, for example cable ties or adhesive tape.

In a preferred embodiment of the reflectance sensor according to the invention, the reference waveguide is led via an attenuating element, that is to say a precise spacing element with incorporated scattering disk, in order to maintain the full aperture angle.

The arrangement of optical waveguides (fiber arrangement) must be carried out such that the reflectance of a liquid pigment preparation can be measured. In the case of reflectance, the light which is reflected diffusely at the interface on the medium side, that is to say at the interface to the measuring window, of a transparent two-dimensional element which terminates the optical waveguide is measured, but, as a rule, the reflection from the interface itself is not measured.

The reflection at the scattering pigments or particles is designated diffuse here (as opposed to the specular reflection at the plate surfaces); this does not mean that this reflection cannot be angle-dependent, such as can be the case in aligned platelets ("gloss angle", "flop").

In principle, the reflectance optical system comprises at least 2 optical waveguides (fibers), possibly lenses, aperture stops, scattering disks, and a common front element which is penetrated both by the light from the illumination fiber and also by the light scattered back by the product (reflectance), on the path to the receiving fiber. This front element is advantageously a plane disk of transparent material but, in principle, can also be implemented as a prism, lens, rod, cylinder or fiber, in the extreme case even as an air pad with or without a film.

In principle, various fiber arrangements are conceivable in the reflectance sensor according to the invention. Preferred fiber arrangements can be determined by those skilled in the art on the basis of the following criteria:

A) Light sensitivity: this has an effect on the required integration time of the sensor. Since the light output from the lamp is limited, the fiber diameter also and the sensitivity of the sensor likewise, integration times between 50 and 2000 ms are typical. 100 to 600 ms are desirable. Integration times longer than 2000 ms are unfavorable, since the dark current component then rises and the signal error increases. The longer measurement time which results (all the more so if the measurement is repeated many times in order to minimize the error) is unfavorable. Cooling the sensor in order to reduce the dark current is very expensive.

B) Stability: a reproducibility of 0.05 to 0.2% of the reflectance is particularly preferred. Depending on the color, this corresponds to a dE of 0.02 to 0.08. (With the reflectance sensors known in the prior art, a reproducibility of 1 to 10% is achieved when measuring liquid samples.) The timescale is in this case in the minutes range, that is to say the deviation between two immediately successive measurements (with the same product, or as compared with the product type), or the time interval between two calibrations (for example 24 hours), and also the long-term stability as a result of repeated calibrations. Critical factors in this case are the ageing of the optical parts and fibers, mechanical displacements, shrinkage and swelling of the materials, creep processes and fatigue as a result of alternating thermal loads, repeatability of mechanical positioning during calibration, ageing and replacement of the light source, wear of the product-contacted surface. The various geometries are not sensitive to the same extent with respect to these factors.

C) Crosstalk attenuation: this means the uncontrolled amount of light getting from the light source to the receiving fiber when an ideal black product is resting on the front disk (measuring window), as related to the amount of light reflected by the reference white (100%, for example white standard or white paste). Here, ratios of 10% ($10^{-1}$) as far as 0.01% ($10^{-1}$) or better can be achieved. Dark products lie around 1% reflectance. Although the background can be subtracted for computation, this penalizes the accuracy. Crosstalk attenuations which lie below the reflectance of the product by a factor beginning at 30, preferably beginning at 100 are preferred.

D) Concentration dependence: colorimetry for coatings and pigment preparations is, within certain limits, independent of the concentration of the pigments. This is true as long as the layer thickness tested is opaque. In the case of conventional color measuring instruments, there is no concentration dependence in the usual area of application in the case of opaque products; that is to say there is no dependence of the reflectance on the penetration depth. Some geometries described here surprisingly exhibit a concentration dependence in some regions.

FIG. 1 illustrates characteristic curves for various sensor heads (geometries). In this case, the wavelength in nm is shown on the abscissa and the relative transmission on the ordinate. The lowest graph (triangles) shows the characteristic curve for the geometry illustrated in FIG. 3, the central graph (diamonds) shows the characteristic curve for the geometry illustrated in FIG. 4, and the top graph (squares) shows the characteristic curve for the geometry illustrated in FIG. 2.

The concentration dependence can be reduced to about 1% with a suitable structure and the remaining 1% can be corrected by computation, so that the concentration dependence does not impair the measurement accuracy.

The fiber arrangement (reflectance geometry) is generally configured by a front element being defined as the starting point of an optical arrangement. The front element in the reflectance sensor according to the invention is the measuring window (Ba). In general, the material, refractive index, thickness and planarity of the measuring window are critical. Thicknesses of the measuring window of, in general, 1 to 12 mm, preferably 2 to 8 mm, particularly preferably 2 to 3 mm, are expedient. The diameter is preferably 10 to 80 mm, particularly preferably 20 to 60 mm, particularly preferably 30 to 50 mm. All optically transparent materials are suitable as material, for example glass (quartz), semi-precious stones (sapphire) or diamond. In this series, increasing hardness is beneficial, unfavorable are the increasing price and the increasing refractive index (more reflections). An internal anti-reflective coating is advantageous for all. The central perpendicular to the measuring window (plate) forms a reference system (plate axis).

The illumination fiber(s) and the receiving fiber(s) are conceptually initially aligned with their mid-axes in accordance with the plate axis, they can then be displaced radially from this axis and rotated tangentially around the axis. In addition, they can be inclined in the radial (and in principle also in the tangential) direction. Use is preferably made of one receiving fiber and one or more illumination fibers. The fibers have aperture angles of about 10°.

Two angles are important above all: the angle between illumination fiber and receiving fiber, and the angle of inclination of the fibers in relation to the plate axis. For good crosstalk attenuation, it is an important aspect to incline the fibers such that the mirror reflection of the illumination fiber (cone of light) on the inside and outside of the measuring window (plate) is not "seen" directly by the receiving fiber. (The first specular reflection can be used with a separate receiving fiber as a reference). This is ensured by suitable geometric constructions. FIGS. 2 to 4 show three possible preferred geometries. All the geometries shown are suitable for the highly accurate reflectance measurement. The geometries in FIGS. 2 and 3 are preferred, the geometry in FIG. 2 is quite particularly preferred.

Figure 2A:
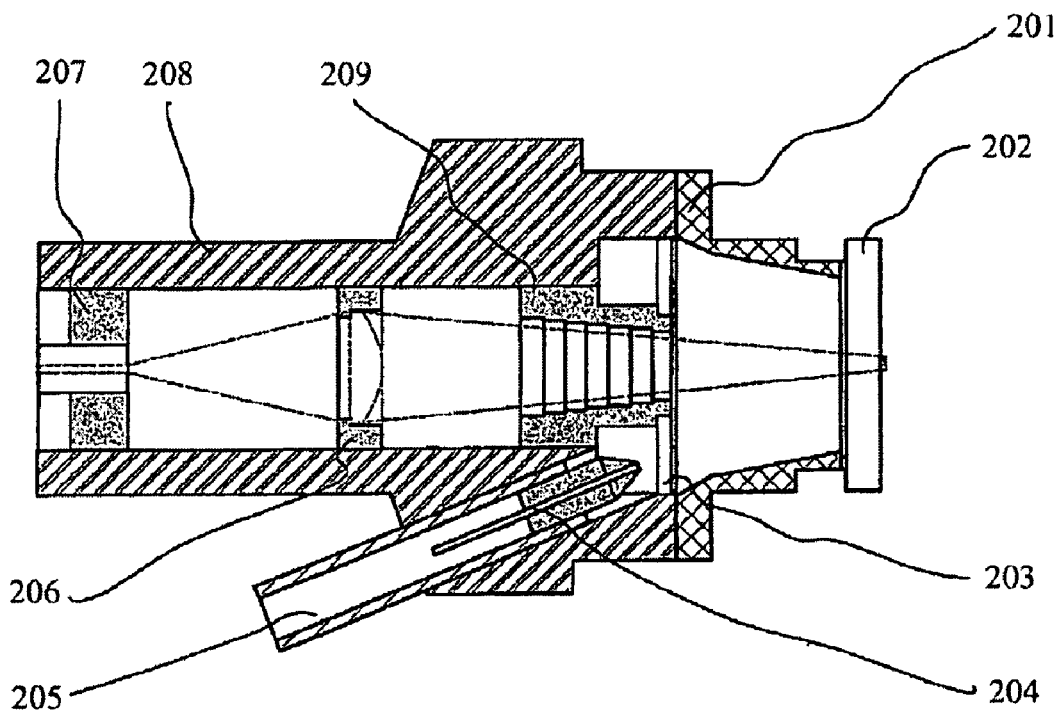
FIGS. 2a and 2b respectively illustrate a side view and a plan view of a geometric construction of illumination and receiving fibers in the reflectance sensor in which the angle between illumination and receiving fiber(s) is 22° and the angle of inclination of the receiving fiber(s) with respect to the plate axis is 0°.
Figure 2B:
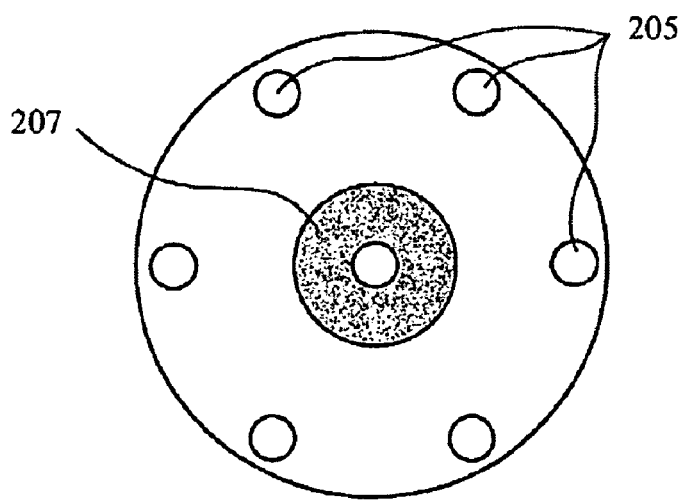

In FIGS. 2a and 2b, a geometric construction of illumination and receiving fibers in the reflectance sensor according to the invention is illustrated in which the angle between illumination and receiving fiber(s) is 22° and the angle of inclination of the receiving fiber(s) with respect to the plate axis is 0°. The illumination fiber(s) are arranged circularly around the receiving fiber(s) (=sensor 0°/22° circular). For the purpose of illumination, use is made of one or more fiber(s), preferably 4 to 12, particularly preferably 6 to 8. In the case of reception or illumination at 0°, the angle between illumination and receiving fibers is generally 5° to 75°, preferably 15° to 65°, particularly preferably 20° to 45°.

In FIG. 2a and 2b:
201 is the adapter for installation
202 the measuring window
203 the scattering disk (optional)
204 the illumination fiber(s)
205 the fiber connector for illumination fiber
206 the lens holder with lens
207 the fiber support with receiving fiber(s)
208 the base body, and
209 the light trap (optional).

FIG. 2a shows a side view of the fiber geometry of the reflectance sensor, and FIG. 2b shows a plan view, it being possible to see the circular arrangement of the illumination fiber(s).

Figure 3A:
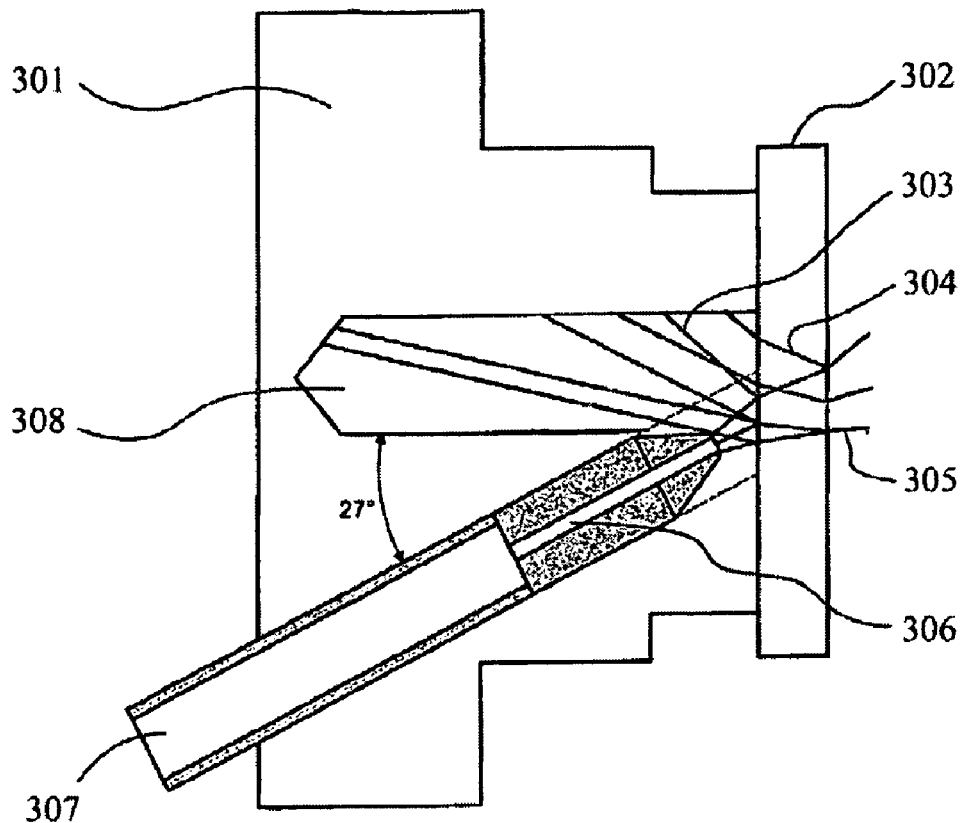
FIGS. 3a and 3b respectively illustrate a side view and a plan view of a geometric construction of illumination and receiving fiber(s) in the reflectance sensor in which the angle between illumination and receiving fiber(s) is 0° and the angle of inclination of the receiving fiber(s) with respect to the plate axis is 27°.
Figure 3B:
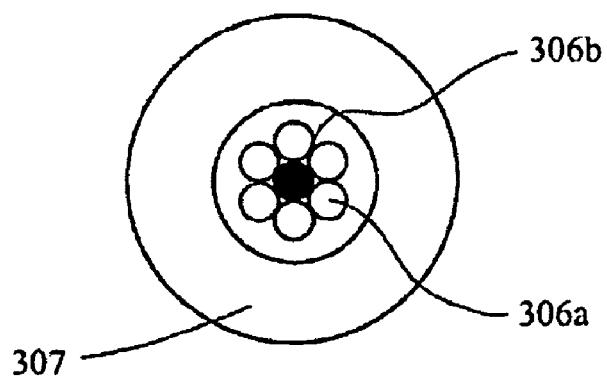

In FIGS. 3a and 3b, a geometric construction of illumination and receiving fiber(s) in the reflectance sensor according to the invention is illustrated in which the angle between illumination and receiving fiber(s) is 0° and the angle of inclination of the receiving fiber(s) with respect to the plate axis is 27°. The illumination and receiving fiber(s) are arranged circularly around the plate axis (sensor 27°/0° circular).

For the purpose of illumination, use is made of one or more fibers, preferably 4 to 12, particularly preferably 6.

In the case of parallel reception and illumination, the angle of inclination between the fiber system and the perpendicular is generally 5° to 75°, preferably 15° to 65°, particularly preferably 20° to 45°.

In FIG. 3a and 3b:
301 is the base body
302 the measuring window
303 the first reflection
304 the second reflection
305 the beam path in the product
306 the fibers
306a the illumination
306b the reception
307 the fiber connector, and
308 the light trap (optional).

FIG. 3a shows a side view of the fiber geometry of the reflectance sensor and FIG. 3b shows a plan view, it being possible to see the circular arrangement of illumination and receiving fiber(s).

Figure 4A:
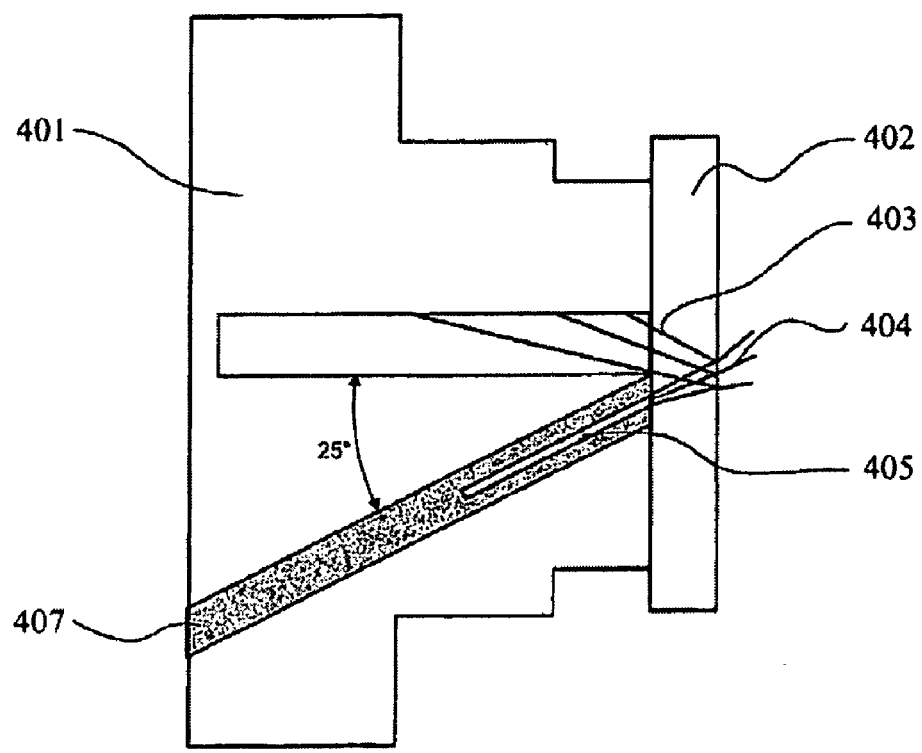
FIGS. 4a and 4b, respectively illustrate a side view and a plan view of a geometric construction of illumination and receiving fibers in the reflectance sensor in which the angle between illumination and receiving fiber(s) is 56° and the angle of inclination of the illumination fiber(s) with respect to the plate axis is 25°.
Figure 4B:
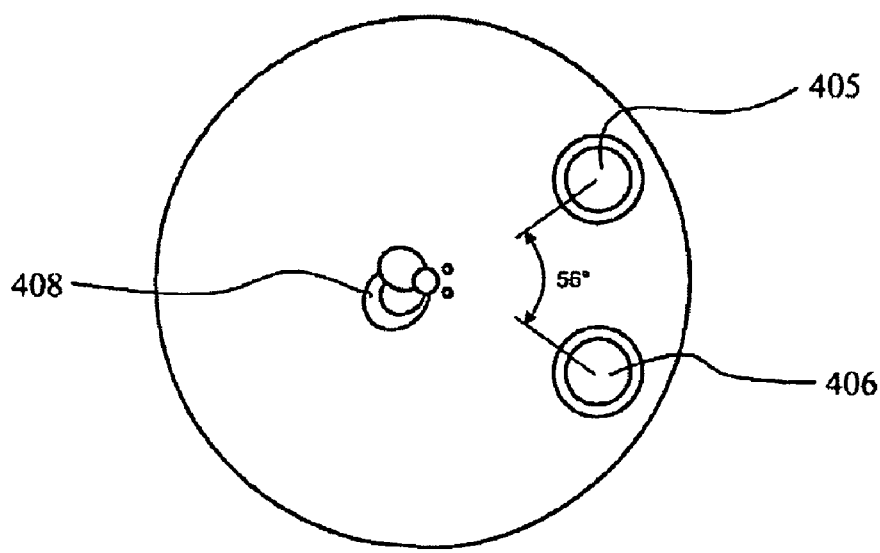

In FIGS. 4a and 4b, a geometric construction of illumination and receiving fibers in the reflectance sensor according to the invention is illustrated in which the angle between illumination and receiving fiber(s) is 56° and the angle of inclination of the illumination fiber(s) with respect to the plate axis is 25° (=sensor 25°/56°).

In the case of geometries with two free angles, the angles can vary in the ranges from, in general, 5° to 75°, preferably 15° to 65°, particularly preferably 20° to 45°, both for the angle of inclination with respect to the perpendicular and for the angle in relation to each other (the two angles do not have to be equal).

Furthermore, the illumination fibers can also be arranged circularly around one or more inclined receiving fiber(s), the intention preferably being here for a smaller angle with respect to the receiving fiber to be used (similar to the geometry in FIGS. 2a and 2b).

In FIG. 4a and 4b:
401 is the base body
402 the measuring window
403 the first reflection
404 the beam path in the product
405 the illumination fiber(s)
406 the receiving fiber(s)
407 the fiber connector, and
408 the light trap (optional).

FIG. 4a shows a side view of the fiber geometry of the reflectance sensor and FIG. 4b shows a plan view, it being possible to see the angle between illumination and receiving fiber(s).

The scattering disk is used to homogenize the light distribution on the object and is not always necessary but is prescribed in the case of various geometries (d/5°=diffusely illuminated with 5° reception).

The base body (support) is a workpiece in which or on which all the small parts are fixed.

The light trap is always used to avoid or suppress light reflections or scattered light and is normally preferred.

However, for the ability to be calibrated well, large angles are disadvantageous. This means that the optimum angles have to be chosen to be sufficiently large that the ability to be calibrated well is still ensured.

Between fiber and measuring window (plate), lenses, aperture stops and scattering disks can also be arranged, with which it is possible to optimize crosstalk, luminous intensity and homogeneity.

It has been found that the concentration dependence is low in the case of low penetration depths if the illumination is carried out from different directions, that is to say concentrically, and in particular the illumination spot is made larger than the observation spot, compatible with a short shearing length according to the invention. The illumination spot is therefore preferably larger than the observation spot. The diameter of the illumination spot is particularly preferably 4 to 20 mm, particular preferably 8 to 14 mm, and the diameter of the observation spot is 1 to 10 mm, particularly preferably 2 to 5 mm. The reflectance sensor according to the invention is thus suitable in particular for exact reflectance measurements on liquid pigment preparations.

Whilst taking these relationships into consideration, the optimum for an application can be determined experimentally in a simple way by those skilled in the art.

In order to connect the optical waveguides (=fibers) to the light source and the detector, commercially available SMA connectors are generally used.

In a particularly preferred embodiment, the reflectance sensor according to the invention according to embodiment (I) or the reflectance sensor according to the invention according to embodiment (II) additionally has at least one of the following features:

ac) arranged behind the lamp is a compensation filter, which linearizes the spectrum from the lamp such that the difference between the highest and lowest intensity of the light emitted by the lamp is as small as possible, for example at most a factor 4, ad) an IR blocking filter, a condenser and a scattering disk are arranged behind the lamp—between lamp and compensation filter if a compensation filter is used, ae) the optical waveguides are led in protective tubes and supported over their entire length by means of a supporting frame, af) the reference waveguide is led via a precise spacing element with incorporated scattering disk, and attenuated in a defined manner.

The individual features according to ac), ad), ae) and af) have already being defined precisely above. The reflectance sensor according to the invention according to embodiment (I) or the reflectance sensor according to the invention according to embodiment (II) preferably additionally has at least the features ac) and ad), quite particularly preferably at least the features ac), ad) and ae), and in particular the features ac), ad), ae) and af).

The optical unit (A) is preferably guided in a precision bore and pressed against the measuring window by a defined spacer.

b) Sample Analysis Unit (B)

The sample analysis unit (B) comprises a measuring window (Ba) and a sample analysis cell (Bb).

The following explanations with respect to the measuring window (Ba) in the reflectance sensor according to the invention for measuring liquid pigment preparations (embodiment (I)) apply likewise to the measuring window (B'a) in the reflectance sensor according to the invention for measuring solid pigmented surfaces (embodiment (II)).

The measuring window (Ba) is generally a plane plate. Suitable materials for the plane plate are all optically transparent materials, for example glass (quartz), semi-precious stones (sapphire) and diamond. The plane plate generally has a thickness from 20 mm, preferably 2 to 10 mm, particularly preferably 4 to 8 mm, and a diameter of in general 10 to 80 mm, preferably 20 to 60 mm, particularly preferably 30 to 50 mm. The plane plate is inserted into a block, preferably a metal block, for example of titanium or stainless steel, so as to be proof against pressure and solvents. For this purpose, the plane plate is, for example, adhesively bonded in or inserted into the block with another joining technique. In one embodiment of the present invention, a plane plate of sapphire has gold vapor deposited on it in order to be introduced so as to be proof against pressure and solvent. The measuring window itself preferably protrudes a few µm, in general 0 to 100 µm, preferably 0 to 50 µm, particularly preferably 10 to 20 µm. The measuring window is generally vertical, so that simple filling of the sample analysis unit with the liquid pigment preparation and simple draining of solvent is possible. The measuring window is preferably round. The metal block (in particular in embodiment (I)) preferably forms a drip edge, in order specifically to form drops at this point of the liquid pigment preparation used as a sample, in order that said drops do not reach sensitive points of the reflectance sensor.

In embodiment (I) of the reflectance sensor according to the invention, the sample analysis cell is arranged on the other side of the measuring window (that is to say on the other side of the measuring window from the optical unit), by said cell being pressed against the measuring window in such a way that, between measuring window and sample analysis cell, a gap is formed which must be traversed by a liquid pigment preparation to be measured, the sample being sheared as it traverses the gap. The shearing is achieved by the pressure loss in the gap preferably being 0.1 to 3 bar over 1 to 15 mm length, particularly preferably 0.5 to 1 bar over 1 to 5 mm length. The fact that the sample analysis cell is pressed onto one side of the measuring window (and can be removed) permits the optical unit and, if appropriate, the measuring window to be cleaned and calibrated easily.

The sample analysis cell is preferably a block in which two bores meet in the front side of the block at an angle of, in general, +/−20° to +/−70°, preferably about +/−45°, with respect to the perpendicular (in this case, "perpendicular" is to be understood to mean the central perpendicular to the plane plate (measuring window)). Exactly in the plane of symmetry of the two bores there is a displacer machined from a cylinder, preferably chamfered in a wedge shape at the front, so that the gap is formed between measuring window and sample analysis cell. This means that, between the measuring window and the displacer, the sample has to traverse a gap which, in general, is 2 to 15 mm, preferably 3 to 5 mm, particularly preferably about 3 mm, long, is 2 to 40 mm, preferably 6 to 25 mm, particularly preferably 8 to 16 mm, wide and, in general, is between 0.05 and 5 mm, preferably between 0.2 and 2.5 mm, particularly preferably between 0.5 and 1.5 mm, high. In this case, the height of the gap can be adjusted variably in a preferred embodiment of the reflectance sensor. In a particularly preferred embodiment of the present application, the sample analysis cell is guided on guide rods, preferably 4, and preferably screwed on with quick-action clamping nuts, particularly preferably 4.

The sample analysis cell can be sealed off with respect to the optical unit in accordance with all methods known to those skilled in the art. In the embodiment of the reflectance sensor in which the height of the gap can be adjusted variably, the displacer can be pushed forward, that is to say in the direction of the measuring window, and locked, preferably by means of a lever. In this case, a defined gap is adjusted by means of spacers (plates) which are preferably labeled. One advantage with this preferred embodiment is that this gap can be changed even when it is filled with products. In an alternative embodiment, the displacer can be adjusted with an electromechanical linear drive unit instead of by a lever.

The considerable shearing of the product in the measuring gap is a decisive factor both in order to obtain a defined sample state, that is to say agglomerates of, for example, pigment particles are broken up by this shearing, and in order to achieve self-cleaning of the measuring window which, as a result of the high shearing of the sample, is continually freed of pigment particles which may have remained stuck to the measuring window. Such shearing of the product and the associated production of a, defined product state, and also self-cleaning of the measuring window, is not mentioned in the prior art.

In a preferred embodiment, the shearing is achieved in that, in the measuring gap, a pressure drop from the entry point of the sample into the gap as far as its exit point of 0.1 to 3 bar over 1 to 15 mm length, preferably 0.5 to 1 bar over 1 to 5 mm length, is produced. A particular advantage of this self-cleaning of the measuring window is that this is also active during the measurement, so that frequent switching on and off of the reflectance sensor for cleaning purposes is rendered superfluous, which is advantageous in particular when the reflectance sensor is used for testing pigment pastes, for example produced during continuous production. Only if the self-cleaning is not adequate in the case of specific products can a wiper additionally be guided over the surface of the measuring window, for example by a Teflon strip being pushed into the gap. This then requires that the gap spacing is adjusted suitably for it, which is possible according to a preferred embodiment of the method according to the invention. In this variant, the gap adjustment is particularly preferably carried out electromechanically.

In order to maintain a defined sample state and therefore to achieve comparable measured data, constant shearing of the sample is necessary. This is preferably implemented by means of continuous monitoring of the input pressure, that is to say the pressure at the entry point of the liquid pigment preparation into the gap.

The pressure monitoring is required in order to achieve defined shearing at the measurement location. If this is ensured by other measures (for example, known pump output, viscosity and gap width), a pressure measurement can be omitted. In the case of a pressure measurement, a plurality of variants are suggested, specifically the T configuration, the V configuration, a measurement with a pressure sensor through which flow takes place, and a bore in the product cell. The construction of the aforementioned configurations is known to those skilled in the art. The selection criterion is the sufficiently accurate measurement of the relatively small pressures, the insensitivity to pressure fluctuations (for example, when the product is delivered by a pulsating pump) and the ability to be flushed easily (no dead spaces) or at least the ability to be cleaned.

In a particularly preferred embodiment of the reflectance sensor according to the invention, the pressure meter is incorporated in a measuring chamber with a very low volume and is protected by a very thin Teflon film against penetration of liquid pigment preparations used as a sample. The feed line is directed upward in a referred embodiment, so that even with a pressure rise of over 2 bar, no product can get into the measuring chamber. As a result, it is merely necessary for the tube to be renewed when a sample change is carried out. The adjustment of the input pressure depends, inter alia, on the hiding power and on the viscosity of the liquid pigment preparation used as the sample. If the sample used is, for example, a coating which does not cover to a great extent, it is necessary to select a larger measuring gap than if a coating which covers more highly is used. The pressure loss then has to be readjusted.

Figure 5:
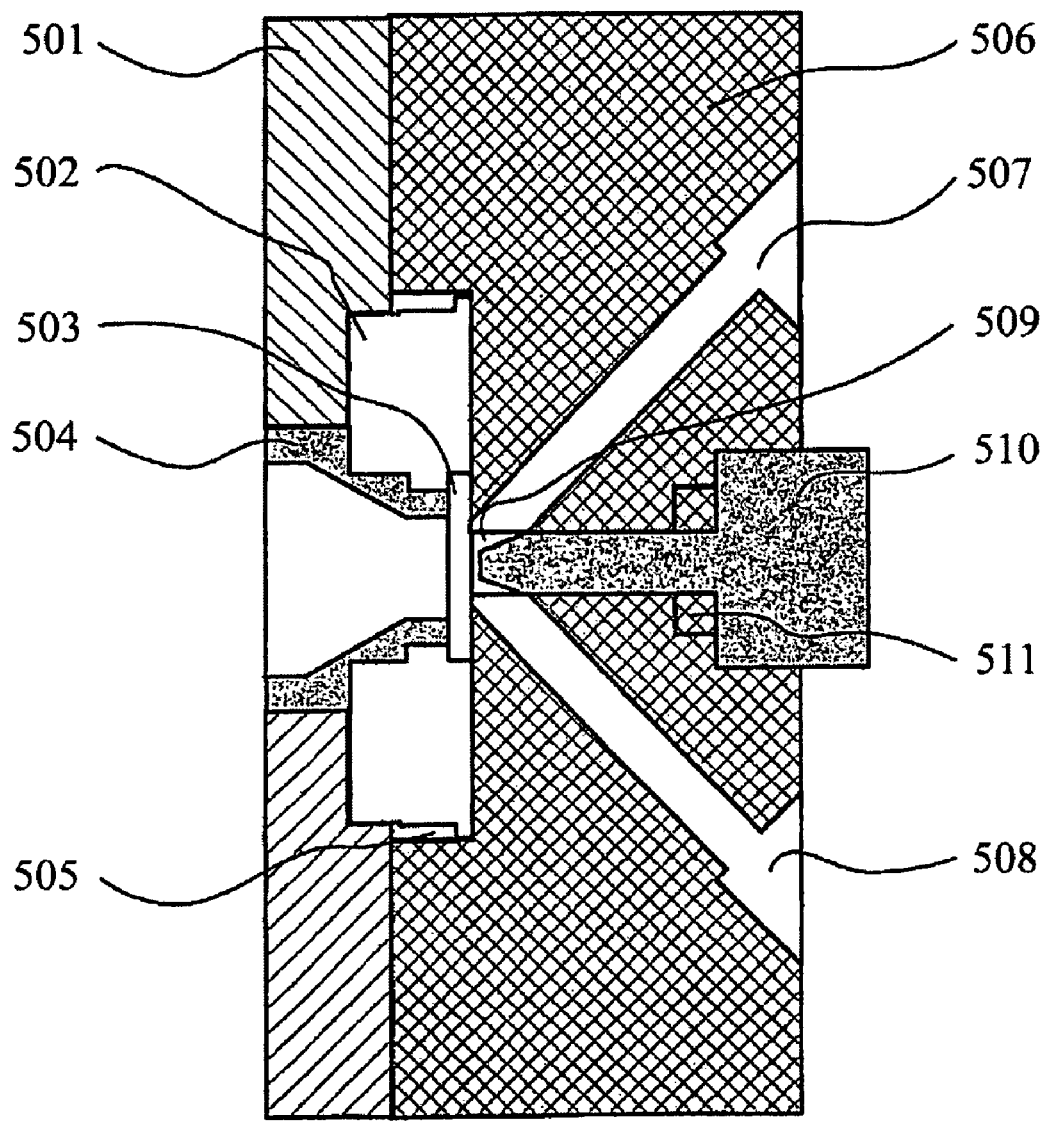
FIG. 5 illustrates an embodiment of a product cell for reflectance measurement on liquid pigment preparations, comprising the sample analysis cell, the measuring window and a holder for the fiber-optic system of the optical unit.

A preferred embodiment of a product cell for reflectance measurement on liquid pigment preparations (wet measurement), comprising the sample analysis cell (Bb), the measuring window (Ba) and a holder (support) for the fiber-optic system (Ab) of the optical unit (A), is illustrated in FIG. 5.

Here:
501 is the base plate (mounting plate)
502 the holder for the measuring window
503 the measuring window
504 the holder (guide element) for the system
505 the drip edge
506 the base body of the product cell
507 the product outlet
508 the product inlet
509 the shearing gap
510 the device for changing the shearing gap, and
511 a variable sealing system.

The sample analysis cell (Bb) can be removed in the reflectance sensor of the invention and replaced by solid samples, for example metal sheets, films, plastic surfaces or by a calibration standard. If the sample analysis cell is removed and there is a holder for samples which have a solid surface (B'b), there is a reflectance sensor according to the invention according to embodiment (II). Thus, with the reflectance sensor according to the invention, it is possible to carry out both wet and dry measurements. As a result, for example a comparison between a solid and a liquid sample of a product, for example a coating, is possible. The reflectance sensor according to the invention thus permits simple comparison of wet and dry measurements.

A further preferred feature of the reflectance sensor according to the invention according to embodiment (I) is thus that the sample analysis cell (Bb) can be removed. In this case, it is possible to remove the sample analysis cell without difficulty and the part of the reflectance sensor which is present after the sample analysis cell has been removed is suitable for measuring solid samples (dry measurement) without rebuilding being necessary on the part of the reflectance sensor which is present after the removal of the sample analysis cell.

A further subject of the present invention is therefore a reflectance sensor (embodiment (II)), built up from
a) an optical unit (A) which comprises
  aa) a light source (Aa) in the form of a lamp with integrated shutter, and
  ab) a fiber-optic system comprising optical waveguides (Ab), at least one optical waveguide being a reference waveguide,
b) a sample analysis unit (B'), which comprises
  b'a) a measuring window (B'a), and
  b'b) a holder for samples which have a solid surface (B'b),
and
c) a system control unit (C) comprising detectors (Ca) for recording measured data and an evaluation device (Cb) connected thereto,
an optical waveguide connection being led from the light source (Aa) to the measuring window (B'a) and from the measuring window (B'a) onward to the detector (Ca), to generate a measured signal, and a reference waveguide connection being led directly from the light source (Aa) to the detector (Ca) or from the measuring window (B'a) to the detector (Ca) to produce a reference signal.

The optical unit (A), the measuring window (B'a) and the system control unit (C) correspond to the optical unit (A), the measuring window (Ba) and the system control unit (C) which have been described with reference to the reflectance sensor according to the invention for measuring liquid pigment preparations (embodiment (I)) or will be described below in relation to the system control unit.

As the holder (B'b) for samples which have a solid surface (=solid samples), that is to say for example for metal sheets, films, plastics or a calibration standard, any holder known to those skilled in the art is suitable. The solid sample is preferably held by guide rods, pressed against the measuring window by a pressure element and sprung by means of a spring element.

The reflectance sensor according to the invention for measuring solid samples can be used for measuring the pigmented surfaces of, for example, metal sheets, films or plastics or for measuring a calibration standard.

Figure 6:
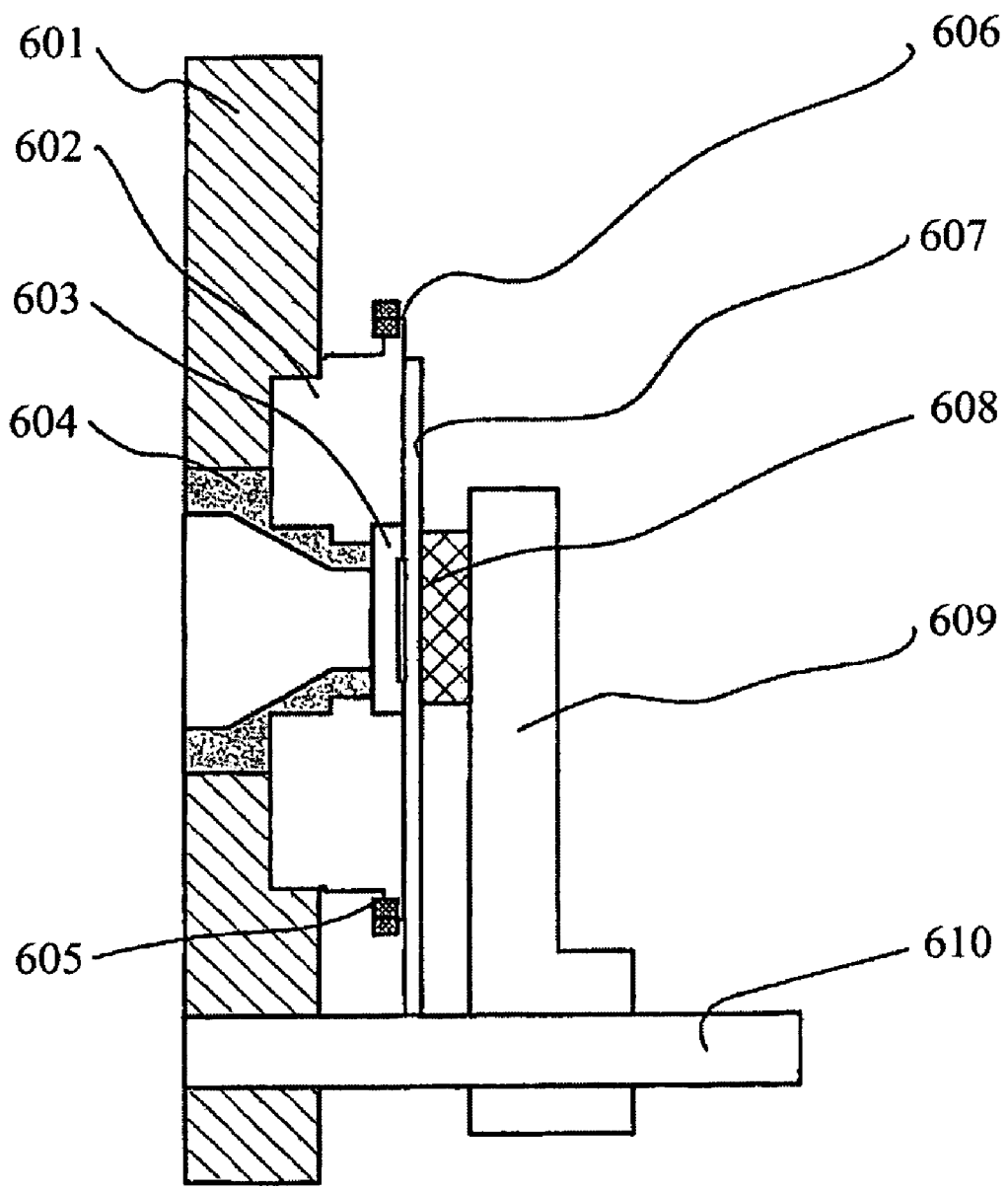
FIG. 6 illustrates an embodiment of what is known as a sheet-metal cell for reflectance measurement on solid pigmented surfaces, comprising the holder for samples which have a solid surface, the measuring window and a holder for the fiber-optic system of the optical unit.

FIG. 6 shows a preferred embodiment of what is known as a sheet-metal cell for reflectance measurement on solid pigmented surfaces (dry measurement), comprising the holder for samples which have a solid surface (B'b), the measuring window (B'a) and a holder (guide element) for the fiber-optic system (Ab) of the optical unit (A).

Here:
601 is the base plate (mounting plate)
602 the holder for the measuring window
603 the measuring window
604 the holder (guide element) for the fiber system
605 the drip edge
606 the spacer
607 the solid sample
608 the spring element
609 the pressure element, and
610 the guide rods.

Figure 7:
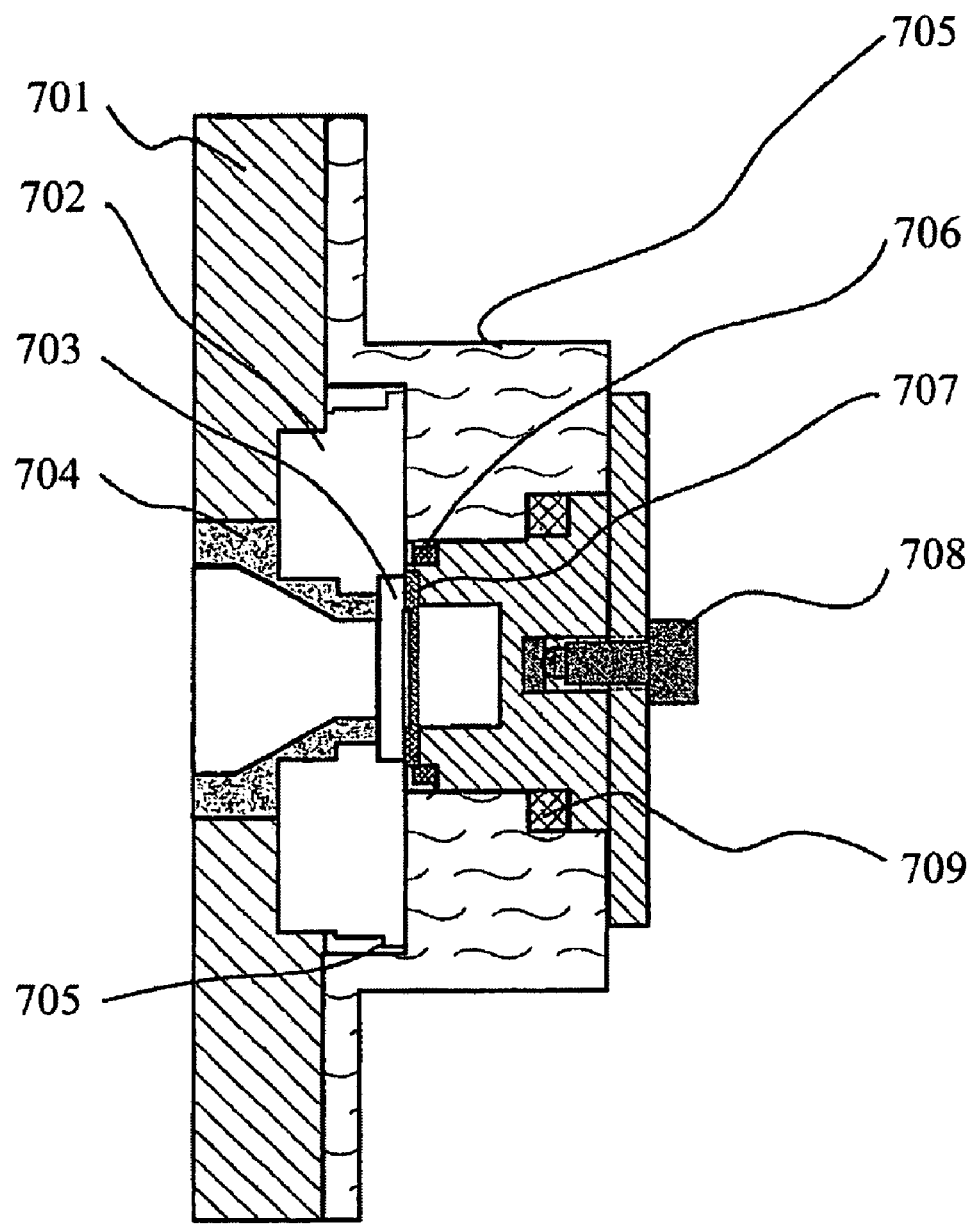
FIG. 7 illustrates an embodiment of what is known as a reference cell for reflectance measurement of the reference standard, comprising the holder for the reference standard, the measuring window and a holder for the fiber-optic system of the optical unit.

FIG. 7 shows a preferred embodiment of what is known as a reference cell for reflectance measurement of the reference standard (preferably a white glass disk) (dry measurement), comprising the holder for the reference standard (B'b), the measuring window (B'a) and a holder (guide element) for the fiber-optic system (Ab) of the optical unit (A).

Here:
701 is the base plate (mounting plate)
702 the holder for the measuring window
703 the measuring window
704 the holder (guide element) for the fibers
705 the drip edge
706 the reference cell base body
707 the spacer
708 the reference standard, and
709 the variable pressure system.

The base plate (support) is a workpiece in which or on which all of the parts are fixed and positioned.

The spacer is used for the accurate and reproducible adjustment of the distance between object and measuring window; this is very important, since the reflectance measurement depends on distance. Contact must be avoided because of interferences.

Hence, the present application comprises various embodiments of reflectance sensors:

a reflectance sensor for measuring liquid pigment preparations (wet measurement) (embodiment (I)), a reflectance sensor for measuring solid pigmented surfaces (dry measurement) (embodiment (II)), a reflectance sensor for calibration ("dry measurement") (embodiment (II)).

The measuring cells of the embodiments are illustrated in FIGS. 5 to 7.

c) System Control Unit (C)

The system control unit comprises detectors for recording measured data and an evaluation device connected thereto. The detectors are preferably fiber-optic monolithic diode-line spectrometers, which permit a resolution of at least 15 bits.

All detectors known to those skilled in the art can be used, and preferably fiber-optically coupled monolithic diode-line spectrometers, since these are very rugged and stable in terms of signals. They should have the highest possible resolution, at least 10 bits, preferably above 12 bits, particularly preferably above 15 bits.

In a particularly preferred embodiment of the reflectance sensor, all the units of the reflectance sensor, that is to say the optical unit, the sample analysis unit and the system control unit, are accommodated in a common housing, in which, preferably, ventilation and thermostat-controlled dissipation of heat, particularly preferably via cooling water, are carried out (cooler/fan). It is preferably a mobile housing which can be transported to the location of use without difficulties, for example a housing on rollers. The housing is temperature-controlled, since a constant temperature leads to an improvement in the measurement accuracy. At the same time, alternating thermal loads are avoided, which can lead to mechanical changes. Furthermore, by means of the housing, contact with the optical waveguides and the other elements of the reflectance sensor is avoided and light-tightness ensured. By means of the common housing, an increase in the measurement accuracy of the reflectance sensor is thus achieved.

One preferred embodiment of the control unit equalizes the brightnesses of the various optical signals (reference, measurement) by using at least one optical attenuator, in order to be able to drive the spectrometer equally and thus at a maximum. This optimizes the measurement accuracy. This attenuator must keep the set attenuation constant and is preferably continuously adjustable and, particularly preferably, by an electromechanical or piezoelectric precision drive. The attenuator has an input for the fiber-optic system and an output to the spectrometer. It can be configured from aperture stops, spacers, scattering disks, conversion filters and neutral filters, but at the same time attention must be paid to stability and maintaining complete aperture illumination.

Figure 8A:
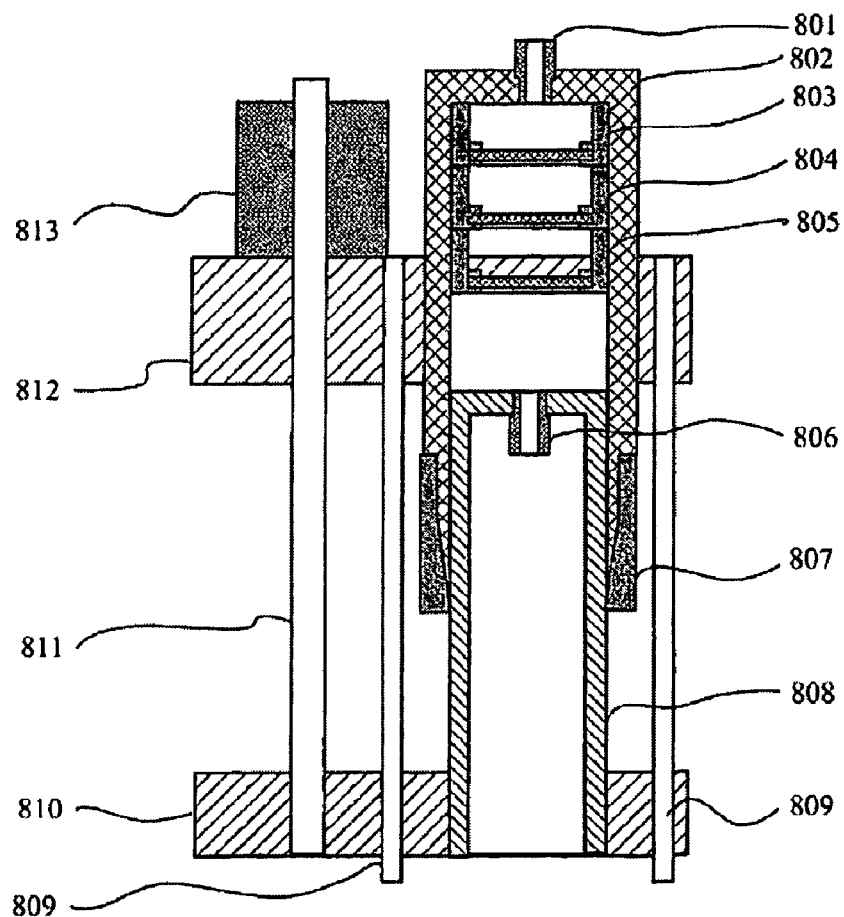
FIGS. 8a and 8b respectively illustrate a front view and a plan view of an embodiment of an attenuator.
Figure 8B:
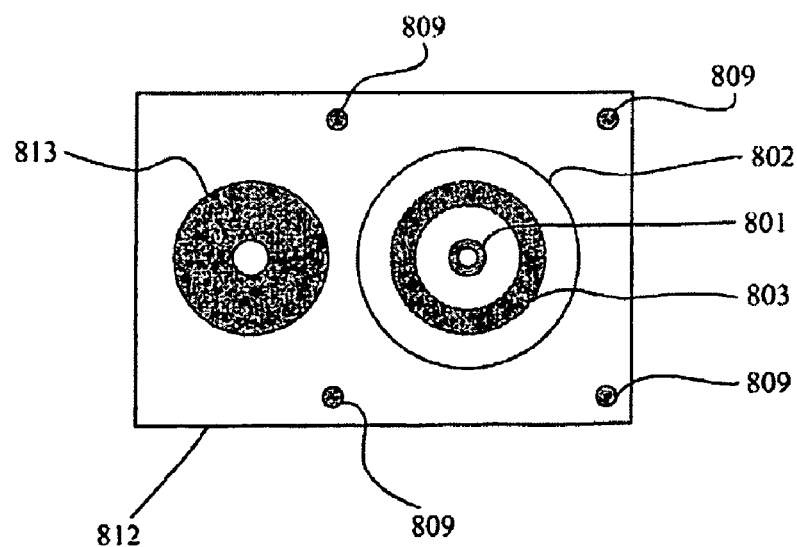

A particularly preferred embodiment of an attenuator is illustrated in FIGS. 8a and 8b.

Here:

801 is an SMA-bush receiving means
802 the base body
803 a scattering disk (optional)
804 a neutral filter (optional)
805 a conversion filter (optional)
806 an SMA-bush transmitter
807 a clamping device
808 a piston
809 guide rods (optional)
810 a carriage (optional)
811 a drive rod (optional)
812 a motor holder (optional), and
813 a motor (optional).

FIG. 8a shows the front view of the attenuator and FIG. 8b the plan view.

FIG. 9 shows a system preferably used for reflectance measurement.

Figure 9A:
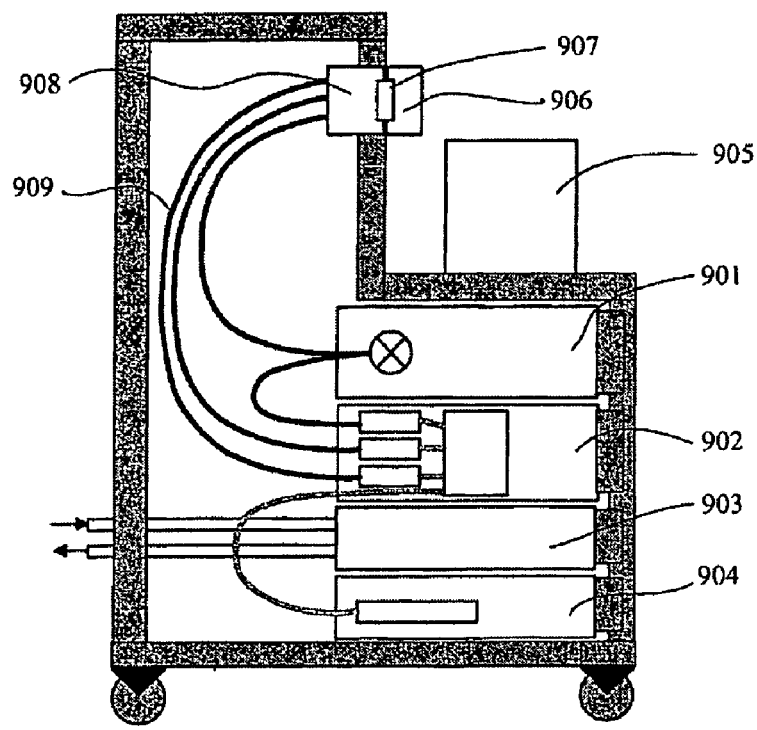
FIGS. 9a and 9b respectively illustrate a side view and a front view of a system used for reflectance measurement.
Figure 9B:
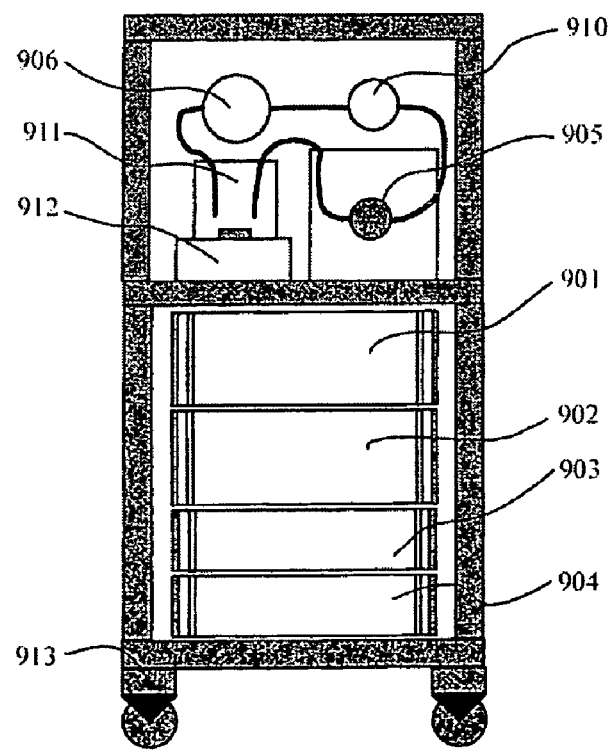

Here, FIG. 9a shows a side view and FIG. 9b a front view. Here:

901 is the light source
902 spectrometers with an optical attenuator (numbers 1 to at most 8) and amplifier
903 a cooler
904 a PC with AD (analog-digital) converter
905 a pump
906 the product cell
907 the measuring window
908 the fiber holder
909 fibers (preferably glass fibers)
910 the pressure measurement
911 a receiver
912 a stirrer (for example a magnetic stirrer), and
913 the mobile housing.

Spectrometers 1—at most 8 means that each light path to be measured has its own spectral detector (spectrometer).

path 1 normally reflectance
path 2 normally reference directly from the lamp
path 3 normally reference from the disk
path 4 optional second reflectance direction
path 5 . . . .

The maximum measurement accuracy of the reflectance sensor (both according to embodiment (I) and according to embodiment (II)) is achieved when all the aforementioned features are fulfilled in the reflectance sensor. Thus, with the aid of the reflectance sensor according to the invention according to embodiment (I) for measuring liquid pigment preparations, very high absolute measurement accuracies of, in general, <0.5 up to 0.05 dE can be achieved, which is achieved by means of an absolute measurement accuracy of 0.1% of the raw measured data (reflectance intensities). In comparison with this, in the case of measurements of solid pigmented surfaces (dry measurements) according to the prior art, absolute measurement accuracies of 0.1 dE are achieved. The reflectance sensor (embodiment (I)) according to the invention is therefore suitable to replace complicated dry measurements. This is achieved by the sensor characteristics of the reflectance sensor according to the invention. In contrast, conventional reflectance sensors according to the prior art merely achieve absolute accuracies of about 1 to 10%. The causes of this are, inter alia, fluctuations in the lamp brightness, fluctuations in the transmission characteristics of the fibers, fluctuations in the dark current, a lack of product renewal at the measurement location, an undefined product state at the measurement location, the growth of baked-on deposits on the measuring window, creeping displacement of residues of other colors from dead spaces in the product feed and fluctuations in the optical detector. These causes are eliminated with the reflectance sensor according to the invention, in particular with the preferred embodiments of the reflectance sensor according to the invention.

Before the start of the measurements, the reflectance sensor (both according to embodiment (I) and according to embodiment (II)) must be calibrated. This can in principle be carried out in any desired manner known to those skilled in the art. A white glass disk is preferably used for the calibration of the reflectance sensor, since this is substantially less susceptible to contamination than a matt surface which is normally used. As compared with the matt surface, the glass has the advantage that it does not age and may always be cleaned again in a defined manner. The reflection of the glass is uncritical, since the reflectance sensor is generally constructed in any case such that specular reflections are masked out. For the purpose of calibration, the sample analysis cell of the reflectance sensor according to embodiment (I) is removed.

In a preferred embodiment, the white glass disk (calibration disk) is guided against the measurement window in a precision holder on the guide rods normally carrying the sample analysis unit in a preferred embodiment, and positioned with register pins. A spacer ensures a defined and reproducible distance of the white glass disk from the measuring window. This distance is advantageously set to values of 50 to 500 µm, particularly preferably about 100 µm. The glass disk and the spacer are mounted resiliently, preferably via a variable pressing system, for example by spring force or an elastomer, so that they always rest flatly with a defined pressing force on the measuring window. The reproducibility of this calibration is around 0.1%.

A further advantage of the reflectance sensor according to the invention is that, using this apparatus, measurements, in particular comparative measurements, can be carried out with pigmented surfaces of solid samples, for example of metal sheets and films, instead of the liquid pigment preparations if the sample analysis cell is replaced by these solid samples, for example metal sheets and films. For this purpose, guide rods, in particular the upper guide rods can be removed. In general, a spacer is slipped over the measuring head (that is to say the measuring window with holder). A metal sheet is placed on the lower rods and is pressed against the measuring window by a pressure element guided by these rods. The pressing is carried out with a resiliently suspended plane plate of the size of the measuring window.

The possibility, using the same optics, of measuring solid samples as well, for example metal sheets, at a defined distance and in a defined alignment, is a special feature of the planar design of the measuring window and of the removable product cell. This possibility permits simple transfer of wet measurements to dry measurements.

A further subject of the present application is a method of measuring the reflectance of a sample in the form of a liquid pigment preparation, comprising:
i) forming a sample stream with a defined thickness,
ii) irradiating the sample stream with electromagnetic radiation emitted by a light source, the electromagnetic radiation interacting with the sample and some of the radiation being reflected diffusely following interaction with the sample,
iii) receiving and registering the diffusely reflected radiation as a reflectance signal,
iv) receiving and registering a reference signal, the reference signal being electromagnetic radiation emitted by the same light source which serves to irradiate the sample stream but which does not interact with the sample,
the reflectance signal and the reference signal being registered simultaneously.

The situation is therefore reached in which both signals, that is to say the reflectance signal and the reference signal, are affected by the same random fluctuations. This is achieved by using fiber-optic monolithic diode-line spectrometers, which preferably permit a resolution of at least 15 bits and which, with integration times between 4 ms and 6000 ms, are matched to the existing brightness. The values measured with such diode-line spectrometers are based on a diode number and must be interpolated to fixed wavelengths. This interpolation is particularly accurate if a spline is used, which is preferred. For this purpose, however, the sensitivity differences of the individual diodes must be compensated for in advance, since otherwise overswings occur. This compensation is carried out by dividing the signals by means of a pattern characteristic of the sensor module before the interpolation.

In a preferred embodiment, the method according to the invention is carried out with the reflectance sensor according to the invention according to embodiment (I). Preferred embodiments of the reflectance sensor according to the invention have already been cited above.

Figure 11:
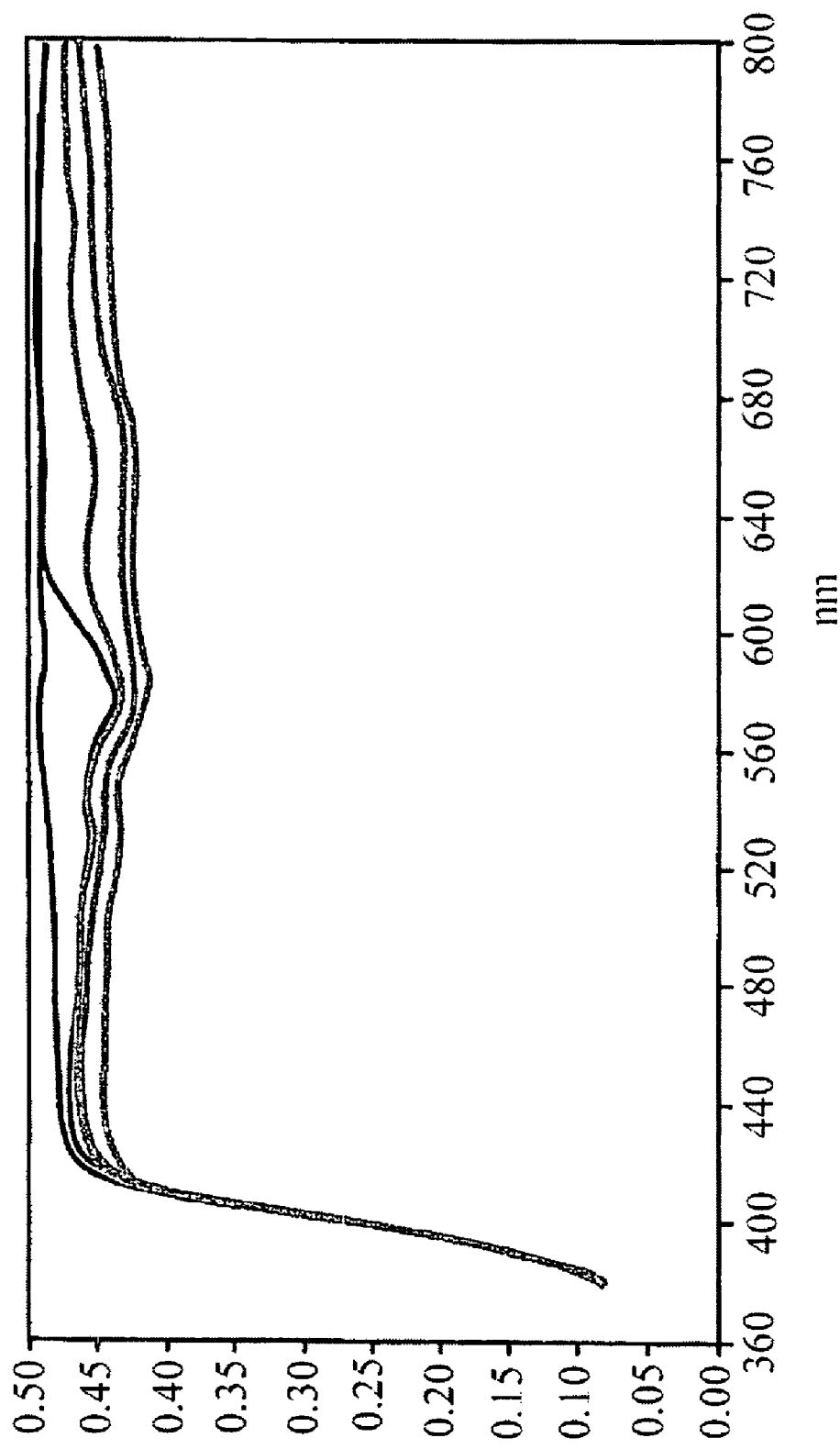
FIGS. 11 and 12 illustrate the results of sensitivity tests where a white coating was mixed with various colored pastes.
Figure 12:
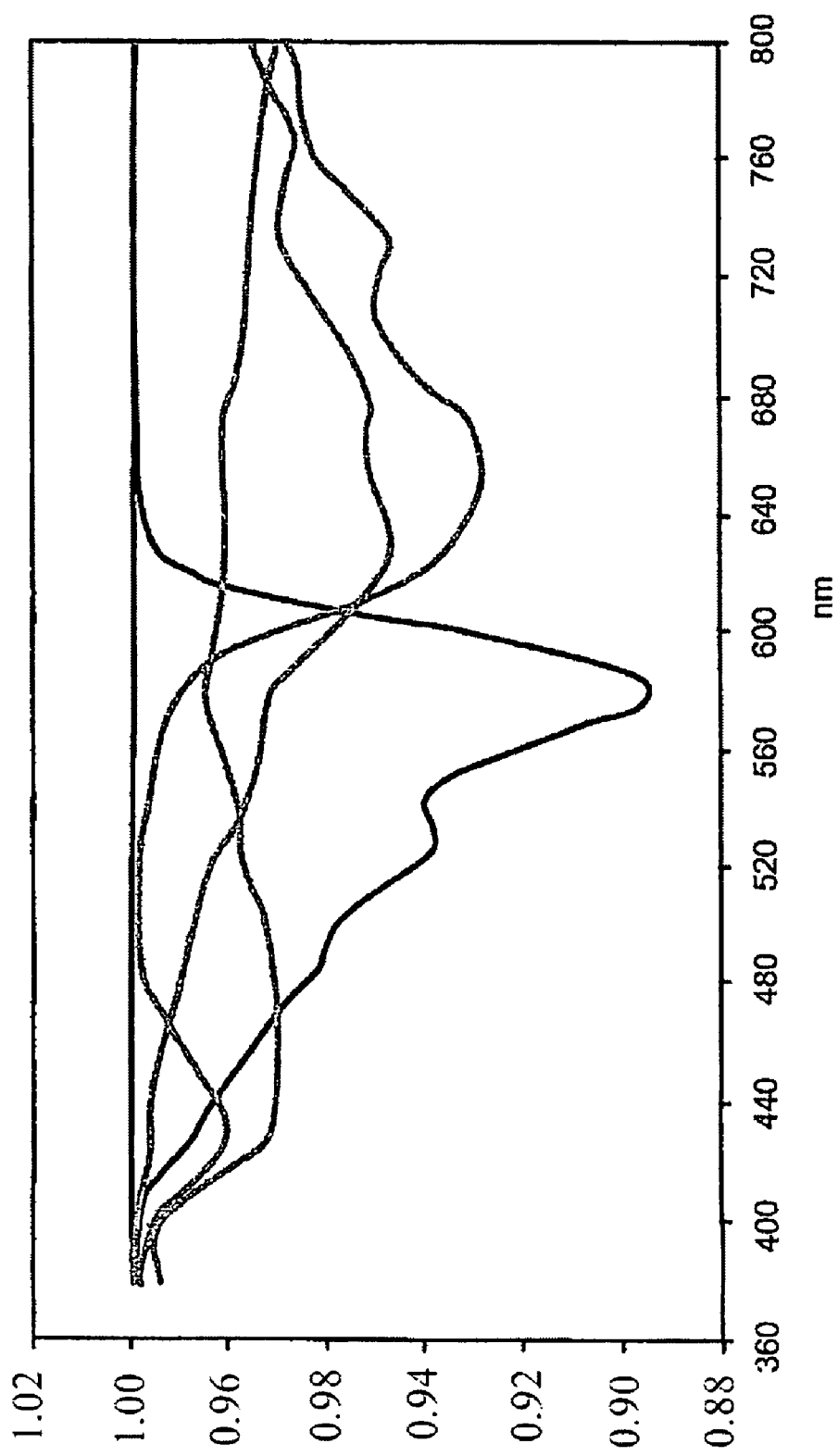

A further subject of the present application is, therefore, the use of the reflectance sensor according to the invention according to embodiment (I) for measuring the reflectance of a sample in the form of a liquid pigment preparation. The results of reflectance measurements with the reflectance sensor according to the invention are illustrated in FIGS. 10 to 12.

Figure 10:
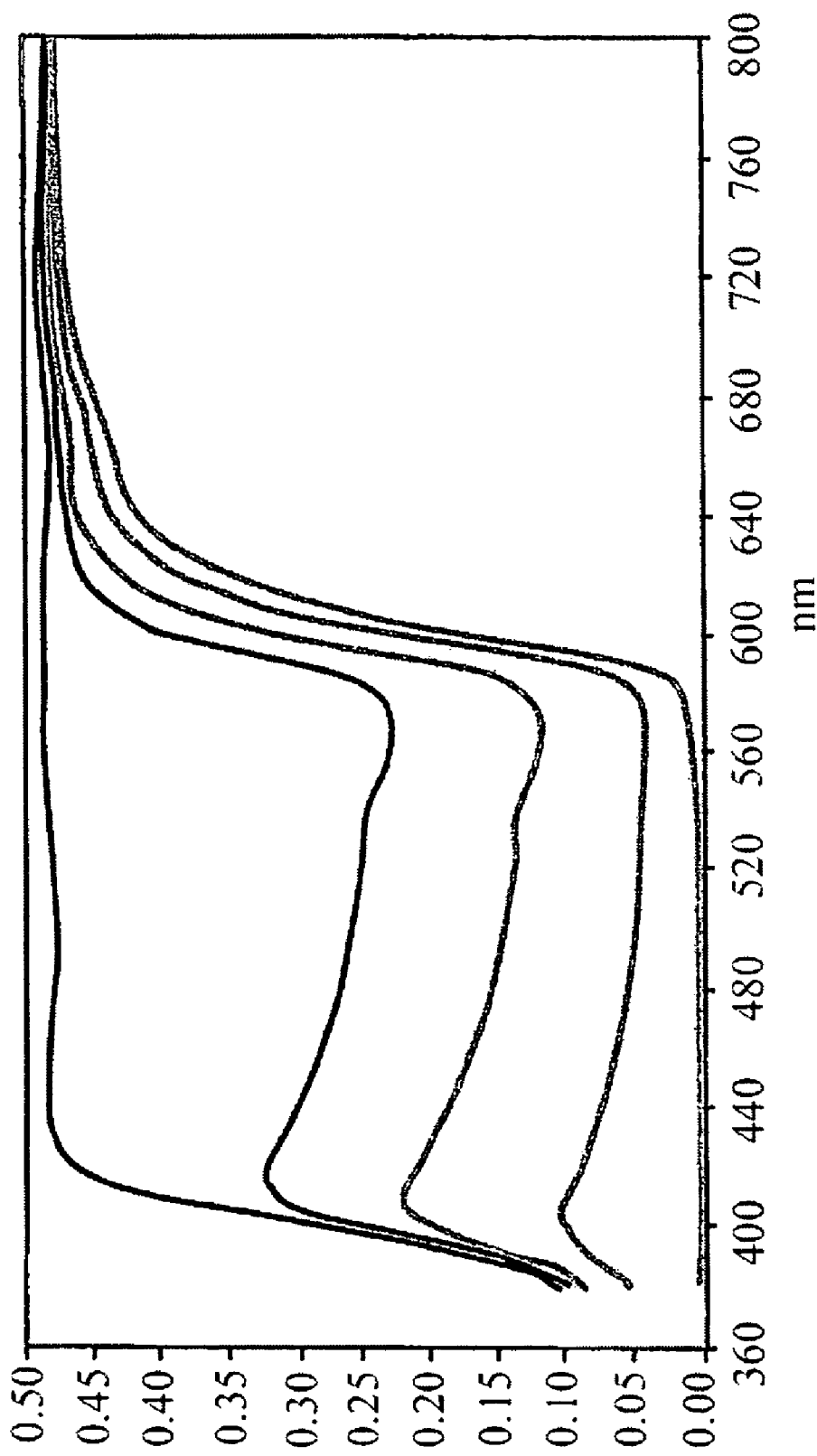
FIG. 10 illustrates the result of a reflectance measurement of a mixture of red with white.

FIG. 10 shows the result of a reflectance measurement of a mixture of red with white.

The wavelength in nm is shown on the abscissa, and the reflectance on the ordinate.

The various graphs represent the measured results in various red/white ratios.

The lowest and brightest graph relates to a preparation of 100% red.

The graph above it relates to a mixture of 70% red and 30% white.

The graph above that relates to a mixture of 9% red and 91% white.

The topmost and darkest graph relates to a preparation of 100% white.

FIG. 11 shows the result of a sensitivity test. For this test, a white coating was mixed with various colored pastes.

The wavelength in nm is shown on the abscissa, and the reflectance on the ordinate.

The lowest graph at a wavelength of 600 nm relates to a white coating with 0.34% black.

The graph above it at a wavelength of 600 nm relates to a white coating with 0.26% blue.

The graph above that at a wavelength of 600 nm relates to a white coating with 0.17% green.

The graph above that at a wavelength of 600 nm relates to a white coating with 0.26% red.

The topmost and darkest graph at a wavelength of 600 nm relates to a pure white coating.

FIG. 12 likewise illustrates the result of a sensitivity test. For this test—as in FIG. 11—a white coating was mixed with various colored pastes.

The wavelength in nm is shown on the abscissa, and the reflectance on the ordinate.

The lowest graph at a wavelength of 420 nm relates to a white coating with 0.34% black.

The graph above it at a wavelength of 420 nm relates to a white coating with 0.17% green.

The graph above that at a wavelength of 420 nm relates to a white coating with 0.26% red.

The graph above that at a wavelength of 420 nm relates to a white coating with 0.26% blue.

The graph above that at a wavelength of 420 nm relates to a pure white coating.

The color of liquid pigment preparations, preferably of liquid coatings, differs considerably from that of the solid pigmented surfaces produced from them, preferably the solid coating film. However, as long as the relationship between the color differences between two liquid pigment preparations, preferably coatings, and the color differences between two solid pigmented surfaces, preferably coating films, is known, in principle a measurement of the liquid pigment preparation, preferably of the liquid coating, is suitable to make a statement about the color of the solid pigmented surfaces, preferably the solid coating film.

In this case, it is a problem that the color at the measurement location in the case of liquid pigment preparations, preferably liquid coatings, is normally not representative of these pigment preparations, preferably this coating, for example on account of agglomeration, sedimentation, specular reflection at moving surfaces, etc.

This then leads to measurements on liquid pigment preparations, preferably liquid coatings, not having sufficient meaningfulness for the solid pigmented surfaces, preferably solid coating films, produced from them.

In principle, therefore, accurate color measurement of the coated object is therefore the most reliable. However, this means a great deal of effort for the production of coated sample panels, associated with the fluctuations which the coating process entails. As a result of providing the reflectance sensors according to the invention, highly accurate measurements of the liquid samples (pigment preparations), preferably coatings, are possible. As a result of the highly accurate measurements, exact correlation of the color of the liquid samples, preferably coatings, with the color of the solid pigmented surfaces obtained from them, preferably of the coating film, is possible.

The reflectance sensor according to the invention can thus, for example, be used in the following applications:

1. Control of the Dispersion Process

During the dispersion of pigmented coatings or pigment pastes, it is nowadays state of the art to stop the process after a specific input of energy or a specific fineness has been reached. For the purpose of quality control, a sample is taken, and an assessment of coated sample panels by hand is frequently required. By measuring the liquid pigment preparations with the reflectance sensor according to the invention, it is possible to dispense with the coating process for assessing the color.

2. Replacement of White Let-downs for Assessing the Quality of Pigment Dispersions In the course of a dispersion, a pigment paste changes its reflectance properties. In particular in the case of dark pigments, however, the reflectance is so low that distinguishing different dispersion states with sufficient accuracy is not possible. Therefore, in practice white pigment is added in order to boost the reflectance. It is possible to dispense with this procedure, which is susceptible to error, if a more accurate and more sensitive method for reflectance measurement is available.

3. Immediate Assessment of the Quality of the Production of Coatings

Assessment of a pigment paste or pigment paste mixture by means of application and measurement of the film properties is frequently not possible, since the pigment paste mixture has not filmed or does not have sufficient hiding power. "Coating on" with other components, needed to form a film, entails additional sources of error. A highly accurate measurement of the liquid pigment paste constitutes a direct and therefore improved relationship between the production process and measured variable. It provides the possibility of assessing the process of coating production on its own without the coating process.

4. Control of a Metering System

The advantage—replacement of the time-consuming production of coated sample panels by simple wet measurement—also applies in the formulation of coatings by mixing various liquids, for example with a metering system. In this case, in order to reach the desired color, the metering process is controlled instead of the dispersion process.

5. Automatically Controlled Color Adjustment During Coating Production

The adjustment of a coating to an exact color, "tinting" (=addition of "auxiliary pigments" for color matching), is carried out nowadays by means of manual sampling, possibly application, measurement, addition of pigment dispersions, in a repeated sequence. Automation of the process with the aid of an in-line reflectance measurement is not possible, because of the inadequate accuracy of the available measuring instruments. A reflectance measuring instrument with high accuracy which can be used in-line would open up the possibility of an automatically controlled tinting process.

6. Color Matching in a Coating System

The color of the coating can also be matched immediately before the coating process, by a metering system for colored pastes being integrated into the coating system (see Color-on-Demand, PPG company), and the control of the additional metering is carried out via a color measurement of the liquid coating which, in this case, should preferably be carried out in-line.

7. Monitoring Subsequent Color Changes

As a result of ageing or shear stressing, pigment pastes or coatings can subsequently change their color. Monitoring the color constancy with a highly accurate measurement method—preferably used in-line—would be helpful.

A further subject of the present application is thus the use of the reflectance sensor according to the invention according to embodiment (I) for the reflectance measurement of liquid pigment preparations in any desired process stage during the production, further processing and use of liquid pigment preparations, preferably for quality control during the dispersion of pigmented coatings and pigment pastes, for quality assessment during coating production, for controlling a metering system during the formulation of coatings by mixing various liquids, for automatically controlled color adjustment by means of tinting during coating production, for matching the color of the coating in a coating system which has a metering system for colored pastes and/or for monitoring subsequent color changes as a result of ageing or shear stressing of pigmented coatings or pigment pastes.

A further subject of the present application is the use of the reflectance sensor according to the invention for carrying out the method according to the invention.

A further subject of the present application is the use of the reflectance sensor according to the invention according to embodiment (II) for the reflectance measurement of a sample which has a solid pigmented surface, for example a metal sheet, a film or a plastic.

With the aid of the reflectance sensor according to the invention according to embodiment (I) and also the method according to the invention, accurate and rapid determination of the reflectance of liquid pigment preparations, in particular of coatings, pigment pastes and white let-downs, is possible and, as compared with the likewise highly accurate measurement (dE ~0.1) on sprayed surfaces, provides a considerable, economically relevant time saving.

The possibility, using the same optics, of measuring solid samples as well, for example metal sheets, at a defined distance and in a defined alignment, is a special feature of the planar design of the measuring window and of the removable product cell. This possibility permits simple transfer of wet measurements to dry measurements.

The invention claimed is:

1. A reflectance sensor, comprising:
an optical unit, comprising:
   a light source comprising a lamp; and
   a fiber-optic system comprising fibers comprising an optical waveguide
   fiber and a reference waveguide fiber;
a sample analysis unit, comprising:
   a measuring window; and
   a removable sample analysis cell; and
a system control unit, comprising:
   a detector for recording measured data; and
   an evaluation device connected thereto;
wherein the optical unit is disposed on a first side of the measuring window and the sample analysis cell is disposed on a second side of the measuring window opposite the first side;
wherein the analysis cell is pressed against the measuring window to form a gap having a pressure drop between the measuring window and the analysis cell,
wherein the gap is traversed by a sample to be measured in the form of a liquid pigment preparation, the sample being sheared by the pressure drop as it traverses the gap,
wherein the optical waveguide fiber extends from the light source to the measuring window, and from the measuring window to the detector, to generate a measured reflectance signal; and
further wherein the reference waveguide fiber extends directly from the light source to the detector or from the measuring window to the detector to produce a reference signal.

2. The reflectance sensor of claim 1, wherein the lamp is selected from the group consisting of LEDs, gas discharge lamps and lamps with incandescent filaments.

3. The reflectance sensor of claim 1, wherein the lamp comprises an integrated shutter.

4. The reflectance sensor of claim 1, wherein the optical waveguide fiber has a diameter of 100 μm, 200 μm, 400 μm, 600 μm, or 800 μm.

5. The reflectance sensor of claim 1, wherein a diameter of the reference waveguide fiber is equal to or smaller than a diameter of the optical waveguide fiber.

6. The reflectance sensor of claim 1, further comprising:
a compensation filter downstream of the lamp, that linearizes a spectrum from the lamp such that a difference between a highest and lowest intensity of the light beam is at most a factor 4;
an IR blocking filter, a condenser and a scattering disk downstream of the lamp;
a protective tube comprising the optical waveguide fiber and a supporting frame that supports the optical waveguide; or
a precise spacing element with an incorporated scattering disk comprising the reference waveguide fiber, and attenuated in a defined manner; or
a combination thereof.

7. The reflectance sensor of claim 1, wherein the measuring window is a 1 to 12 mm thick and 10 to 80 mm in diameter plane plate, the plane plate selected from the group consisting of glass, semi-precious stones and diamond.

8. The reflectance sensor of claim 1, wherein a length of the gap is 2 to 15 mm, a width of the gap is 2 to 40 mm, and a height of the gap is variably adjustable between 0.05 and 5 mm.

9. A reflectance sensor, comprising:
an optical unit, comprising:
   a light source comprising a lamp; and
   a fiber-optic system comprising fibers comprising an optical waveguide fiber and a reference waveguide fiber;
a sample analysis unit, comprising:
   a measuring window; and
   a removable sample analysis cell; and
a system control unit, comprising:
   a detector for recording measured data; and
   an evaluation device connected thereto;
wherein the optical unit is disposed on a first side of the measuring window and the sample analysis cell is disposed on a second side of the measuring window opposite the first side;
wherein the analysis cell is pressed against the measuring window to form a gap having a pressure drop between the measuring window and the analysis cell,
wherein the gap is traversed by a sample to be measured in the form of a liquid pigment preparation, the sample being sheared by the pressure drop as it traverses the gap;
wherein the optical waveguide fiber extends from the light source to the measuring window, and from the measuring window to the detector, to generate a measured reflectance signal;
wherein the reference waveguide fiber extends directly from the light source to the detector or from the measuring window to the detector to produce a reference signal; and
wherein the sample is sheared by a pressure drop of 0.1 to 3 bar in the gap over a length of 1 to 15 mm from an entry point to an exit point of the sample.

10. The reflectance sensor of claim 1, wherein the system control unit comprises detectors consisting of fiber-optic monolithic diode-line sensors that provide a resolution of at least 15 bits.

11. The reflectance sensor of claim 1, disposed in a common housing comprising a ventilation and a thermostat-controlled heat dissipation.

12. A method of measuring a reflectance of a liquid pigment preparation with a reflectance sensor, the reflectance sensor comprising:
an optical unit, comprising:
   a light source comprising a lamp; and
   a fiber-optic system comprising fibers comprising an optical waveguide
   fiber and a reference waveguide fiber;
a sample analysis unit, comprising:
   a measuring window; and
   a removable sample analysis cell; and
a system control unit, comprising:
   a detector for recording measured data; and
   an evaluation device connected thereto;
wherein the optical unit is disposed on a first side of the measuring window and the sample analysis cell is disposed on a second side of the measuring window opposite the first side;
wherein the analysis cell is pressed against the measuring window to form a gap between the measuring window and the analysis cell, wherein the gap is traversed by a sample to be measured in the form of a liquid pigment preparation, the sample being sheared considerably as it traverses the gap, wherein the optical waveguide fiber extends from the light source to the measuring window, and from the measuring window to the detector, to generate a measured reflectance signal; and further wherein the reference waveguide fiber extends directly from the light source to the detector or from the measuring window to the detector to produce a reference signal;

the method comprising:

forming a sample stream with a defined thickness in the gap, the sample consisting of the liquid pigment preparation;

introducing a pressure drop into the gap;

shearing the sample stream in the gap with the pressure drop;

irradiating the sample stream with electromagnetic radiation emitted by the light source, the electromagnetic radiation interacting with the sample and some of the radiation being reflected diffusely following interaction with the sample;

receiving and measuring the diffusely reflected radiation as the measured reflectance signal;

receiving and measuring electromagnetic radiation emitted by the light source which does not interact with the sample as the reference signal;

the measured reflectance signal and the reference signal being measured simultaneously.

13. The method of claim 12, wherein:

measuring the reflectance of the liquid pigment preparation is during a process stage in the production of the liquid pigment preparation, further processing of the liquid pigment preparation, or use of the liquid pigment preparation;

wherein the process stage comprises quality control during the dispersion of pigmented coatings and pigment pastes, quality assessment during coating production, controlling a metering system during formulation of coatings by mixing various liquids, automatically controlling color adjustment by means of tinting during coating production, matching a color of a coating in a coating system that comprises a metering system for colored pastes, or monitoring subsequent color changes as a result of ageing or shear stressing.

14. A reflectance sensor for measuring a sample, comprising:

an optical unit having a light source and a fiber-optic system having an optical waveguide fiber and a reference waveguide fiber;

a sample analysis unit having a measuring window and a removable sample analysis cell; and a system control unit having a detector for recording measured data, the optical waveguide fiber extending from the light source to the measuring window, and from the measuring window to the detector to generate a measured reflectance signal, the reference waveguide fiber extending from the light source to the detector or from the measuring window to the detector to produce a reference signal, the analysis cell located against the measuring window and forming a gap therebetween, that includes a pressure drop between the measuring window and the analysis cell, the gap adapted to be traversed by the sample in the form of a liquid pigment preparation, the sample being sheared by the pressure drop as it traverses the gap.

15. A method of measuring a reflectance of a liquid pigment preparation with a reflectance sensor the method comprising:

forming a sample stream with a defined thickness in a gap between a measuring window and an analysis cell of the reflectance sensor, the sample comprising the liquid pigment preparation;

introducing a pressure drop into the gap;

shearing the sample stream in the gap with the pressure drop;

irradiating the sample stream with electromagnetic radiation emitted by a light source, the electromagnetic radiation interacting with the sample and some of the radiation being reflected diffusely following interaction with the sample;

receiving and measuring the diffusely reflected radiation as a measured reflectance signal;

receiving and measuring electromagnetic radiation emitted by the light source which does not interact with the sample as a reference signal; and simultaneously measuring the reflectance signal and the reference signal.

* * * * *